United States Patent
Lewis et al.

(10) Patent No.: US 12,011,428 B2
(45) Date of Patent: Jun. 18, 2024

(54) COMPOSITIONS AND METHODS FOR STIMULATING VENTILATORY AND/OR RESPIRATORY DRIVE

(71) Applicant: CASE WESTERN RESERVE UNIVERSITY, Cleveland, OH (US)

(72) Inventors: Stephen J. Lewis, Cleveland, OH (US); Michael W. Jenkins, Cleveland, OH (US); James M. Seckler, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 17/696,204

(22) Filed: Mar. 16, 2022

(65) Prior Publication Data

US 2023/0338319 A1 Oct. 26, 2023

(51) Int. Cl.
*A61K 31/198* (2006.01)
*A61K 45/06* (2006.01)
*A61P 11/00* (2006.01)

(52) U.S. Cl.
CPC ............ *A61K 31/198* (2013.01); *A61K 45/06* (2013.01); *A61P 11/00* (2018.01)

(58) Field of Classification Search
CPC .................................................. A61K 31/198
See application file for complete search history.

(56) References Cited

U.S. PATENT DOCUMENTS

| | | | |
|---|---|---|---|
| 10,881,633 B2 | 1/2021 | Gaston et al. | |
| 2002/0002136 A1* | 1/2002 | Hebert | A61K 38/063 514/6.9 |

OTHER PUBLICATIONS

Jenkins et al. Scientific Reports, 2021, 11:6985.*
Srivastava, A. Benjamin, John J. Mariani, and Frances R. Levin. "New directions in the treatment of opioid withdrawal." The Lancet 395.10241 (2020): 1938-1948.
Mendoza, J., et al.; "l-Cysteine ethyl ester reverses the deleterious effects of morphine on, arterial blood-gas chemistry in tracheotomized rats"; Respiratory Physiology & Neurobiology, (2013) 189(1), 136-143. doi:10.1016/j.resp.2013.07.007.
Jenkins, Michael W., et al. "Glutathione ethyl ester reverses the deleterious effects of fentanyl on ventilation and arterial blood-gas chemistry while prolonging fentanyl-induced analgesia." Scientific reports 11.1 (2021): 1-15.
Zeevalk, G. D., et al. "Characterization of intracellular elevation of glutathione (GSH) with glutathione monoethyl ester and GSH in brain and neuronal cultures: relevance to Parkinson's disease." Experimental neurology 203.2 (2007): 512-520.
Kahl, Anja, et al. "Critical role of flavin and glutathione in complex I-mediated bioenergetic failure in brain ischemia/reperfusion injury." Stroke 49.5 (2018): 1223-1231.
Kimura, Hideo. "Hydrogen sulfide: from brain to gut." Antioxidants & redox signaling 12.9 (2010): 1111-1123.
Peng, Ying-Jie, et al. "H2S mediates O2 sensing in the carotid body." Proceedings of the National Academy of Sciences 107.23 (2010): 10719-10724.
Macchia, Iole, et al. "Increased replication of Sendai virus in morphine-treated epithelial cells: evidence for the involvement of the intracellular levels of glutathione." International journal of immunopharmacology 21.3 (1999): 185-193.
Reed, Tanea T., et al. "Proteomic identification of nitrated brain proteins in traumatic brain-injured rats treated postinjury with gamma-glutamylcysteine ethyl ester: insights into the role of elevation of glutathione as a potential therapeutic strategy for traumatic brain injury." Journal of neuroscience research 87.2 (2009): 408-417.
Aberoumandi, Seyed Mohsen, et al. "Heroin-based crack induces hyperalgesia through β-arrestin 2 redistribution and phosphorylation of Erk1/2 and JNK in the periaqueductal gray area." Neuroscience letters 698 (2019): 133-139.
Henderson, M., "Neuroproteomic study of nitrated proteins in moderate traumatic brain injured rats treated with gamma glutamyl cysteine ethyl ester administration post injury: Insight into the role of glutathione elevation in nitrosative stress"; PROTEOMICS—Clinical Applications, 10(12), (2016); 1218-1224. doi: 10.1002/prca.201600004.
Yeung, David T., et al. "National Institutes of Health (NIH) Executive Meeting Summary: Developing Medical Countermeasures to Rescue Opioid-Induced Respiratory Depression (a Trans-Agency Scientific Meeting)—Aug. 6/7, 2019." Journal of Medical Toxicology. vol. 16. No. 1. Springer US, 2020.

* cited by examiner

*Primary Examiner* — Rei Tsang Shiao
(74) *Attorney, Agent, or Firm* — TAROLLI, SUNDHEIM, COVELL & TUMMINO, LLP

(57) ABSTRACT

A method of stimulating ventilatory and/or respiratory drive in a subject in need thereof includes administering to the subject a therapeutically effective amount of a composition comprising an glutathione alkyl ester, adduct thereof, or pharmaceutically acceptable salt, tautomer, or solvate thereof.

9 Claims, 6 Drawing Sheets

COMPOSITIONS AND METHODS FOR STIMULATING VENTILATORY AND/OR RESPIRATORY DRIVE

TECHNICAL FIELD

Embodiments described herein relate to compositions and methods of stimulating ventilatory and/or respiratory drive in a subject in need thereof, and particularly relates to compositions and methods of treating breathing diseases and/or disorders associated with impaired ventilatory and/or respiratory drive.

BACKGROUND

Normal control of breathing is a complex process that involves the body's interpretation and response to chemical stimuli, such as carbon dioxide, pH and oxygen levels in blood, tissues, and the brain. Breathing control is also affected by wakefulness (i.e., whether the patient is awake or sleeping). Within the brain medulla there are respiratory control centers that interpret the various signals that affect respiration and issue commands to muscles that perform the work of breathing. Key muscle groups are located in the abdomen, diaphragm, larynx, pharynx and thorax. Sensors located centrally and peripherally provide input to the brain's central respiration control areas that enable response to changing oxygen requirements.

Normal respiratory rhythm is maintained primarily by the body's rapid response to changes in carbon dioxide levels ($CO_2$). Increased $CO_2$ levels signal the body to increase breathing rate and depth resulting in higher oxygen levels and subsequent lower $CO_2$ levels. Conversely, low $CO_2$ levels can result in periods of apnea (no breathing) since the stimulation to breathe is absent. This is what happens when a person hyperventilates. Additionally, low blood oxygen levels stimulate respiratory drive, and this mechanism can become the primary driver in patients with chronically high $PCO_2$ levels.

Impaired ventilatory drive can complicate a broad spectrum of diseases in pulmonary, sleep, and critical care medicine. Patients with various forms of chronic obstructive pulmonary disease (COPD), among which can be considered late-stage cystic fibrosis (CF), can have impaired ventilatory responses when treated with oxygen or narcotics. In obstructive sleep apnea (OSA), intermittent hypoxia associated with impaired short- and long-term facilitation of hypoxic ventilatory drive and with loop gain may predispose to perioperative complications and adverse neurocognitive sequelae. A variety of other conditions with components of disordered ventilatory control—ranging from congestive heart failure (CHF) to Arnold-Chiari malformation can only be managed with mechanical ventilation. Additionally, endotracheally-intubated patients in the critical care setting who require narcotics for pain control can become unmanageable if narcotic use is stopped but can fail extubation because of respiratory depression if the narcotic is continued. These pulmonary and critical care issues can be all the more challenging in patients with underlying COPD, CF, CHF, OSA and other conditions affecting ventilatory drive.

Few medications are effective as respiratory stimulants. Methylxanthines can be effective in patients with apnea of prematurity but are often ineffective in older patients. Almitrine can transiently improve ventilatory drive in adults with COPD. However, the administration of almitrine is associated with the development of pulmonary arterial hypertension and peripheral neuropathy; and it does not affect outcome.

Conditions associated with impaired ventilatory drive are common and have a substantial public health impact. For example, large, population-based studies report a prevalence of moderate-severe obstructive sleep apnea of 2-14% of the American population—depending on age and gender—and prevalence may be higher (up to 38% of men) in pulmonary clinic. A significant proportion of patients with OSA have impaired ventilatory drive, particularly those who also have heart failure. There is a large, unmet need for a safe and effective respiratory stimulant in pulmonary and critical care medicine.

Additionally, commonly used narcotic and benzodiazepine medications suppress ventilatory drive. Specifically, they depress the slope of the relationship between $PCO_2$ and minute ventilation. This is a major issue in several important settings. In the operating room and post-anesthesia care setting, patients may have prolonged respiratory depression associated with pain control. This results in prolonged hospitalizations or early, risky discharge and death. In the chronic pain population—in the Veteran's Administration system, for example—death from nocturnal respiratory depression is at epidemic proportions among patients on chronic opiate therapy. Opiate addiction is also at epidemic levels, and hundreds of young people die annually without an effective emergency respiratory stimulant. On the battlefield, medics can have to choose between excruciating pain and risk of death from respiratory depression. In the Intensive Care population, physicians often have to choose between the risk of being on the ventilator for one or more days and the risk of awaking a patient in pain and distress. This is a problem in patients with a baseline blunted $CO_2$ response, such as patients with severe COPD, CF or other obstructive lung disease.

Emergency treatment for narcotic-induced respiratory depression is limited largely to the use of narcotic antagonists, such as naloxone or nalmefene, which are effective at reversing the narcotic induced respiratory depression but also reverse the narcotic mediated pain control, exacerbating the original problem. Further, this treatment is specific to narcotics and is ineffective for benzodiazepine or other sedative or anesthetic induced respiratory depression. A respiratory stimulant that overcomes respiratory depression from any source is needed to address these needs.

SUMMARY

Embodiments described herein relate to compositions and methods of stimulating ventilatory and/or respiratory drive in a subject in need thereof, and particularly relates to the use of a glutathione alkyl ester, adducts thereof, and/or a pharmaceutically acceptable salt, tautomer, or solvate thereof in compositions and methods of treating breathing diseases and/or disorders associated with impaired ventilatory and/or respiratory drive.

In some embodiments, the methods can include stimulating ventilatory and/or respiratory drive in a subject in need thereof by administering to the subject a therapeutically effective amount of a composition that includes a glutathione alkyl ester, adduct thereof, and/or pharmaceutically acceptable salt, tautomer, or solvate thereof. The therapeutically effective amount can be an amount effective to stimulate the ventilatory and/or respiratory drive of the subject, including, for example, increasing tidal volume, increasing respiratory frequency, increasing minute ventilation, increasing peak inspiratory flow, increasing inspiratory drive, and/or increasing Alveolar-arterial (A-a) gradient.

The composition can be administered to the subject systemically by, for example, topical (e.g., inhalation), enteral (e.g., oral), and/or parenteral (e.g., intravenous injection) administration.

In some embodiments, the glutathione alkyl ester can include a compound having the structure of formula:

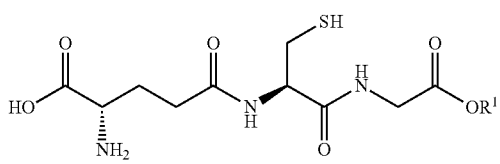

where $R^1$ is a lower alkyl ($C_1$-$C_6$ alkyl); or a pharmaceutically acceptable salt, tautomer, or solvate thereof.

In some embodiments, the glutathione alkyl ester can be an L-glutathione alkyl ester, such as an L-glutathione methyl ester or an L-glutathione ethyl ester, an adduct thereof, or a pharmaceutically acceptable salt, tautomer, or solvate thereof.

In other embodiments, the pharmaceutically acceptable salt of a glutathione alkyl ester is a hydrochloride salt.

In still other embodiment, the adduct of the glutathione alkyl ester can include at least one of an albumin adduct, a glucose adduct, an L-cysteine adduct, a D-cysteine adduct, or an S-nitroso adduct.

In some embodiments, the subject can have or is at increased risk of a breathing disorder, such as respiratory depression, including narcotic, sedative, and/or anesthetic, induced suppression of respiratory drive or ventilatory drive, sleep apnea (central, mixed and obstructive including but not limited to co-existing conditions of heart failure, kidney disease and stroke), sleep-disordered breathing (especially with snoring and arousals), apnea of prematurity, allergies, neurological or neuromuscular diseases (e.g., stroke or amyotrophic lateral sclerosis (ALS)), weakened respiratory muscles, hypoventilation due to stroke, trauma, surgery and/or radiation, obesity-hypoventilation syndrome, primary alveolar hypoventilation syndrome, acquired central hypoventilation syndromes (ACHS), congenital central hypoventilation syndromes (CCHS), chronic bronchitis, Cheyne-Stokes respiration, dyspnea, altitude sickness or acclimatization to high altitude, hypopnea, hypoxia, hypercapnia, cystic fibrosis, chronic obstructive pulmonary disease (COPD), nasal septum deformation, tonsillitis, adenoiditis, and Arnold-Chiari syndrome.

In some embodiments, the composition can be administered to the subject to treat the breathing disorder. For example, the composition can be administered to the subject at an amount effective to prevent the need for mechanical ventilation in subjects with acutely impaired ventilatory and/or respiratory drive because of an acute exacerbation of an underlying lung disease or an acute requirement for narcotic analgesia.

In other embodiments, the subject can have or has an increased risk of respiratory depression that is caused, for example, by an anesthetic, a sleeping aid, a sedative, anxiolytic agent, a hypnotic agent, alcohol, and/or a narcotic. In some embodiments, the narcotic can include an opioid, such as morphine or fentanyl.

In still other embodiments, the composition can be administered to a subject in combination with at least one additional therapeutic agent that changes normal breathing in a subject. The additional agent can be selected from the group consisting of an opioid, doxapram and enantiomers thereof, acetazolamide, almitrine, GAL021, theophylline, caffeine, methylprogesterone and related compounds, sedatives that decrease arousal threshold in sleep disordered breathing patients, sodium oxybate, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, and combinations thereof.

In yet another embodiment, the composition and the agent are separately administered to the subject. In yet another embodiment, the compound and the agent are co-administered to the subject.

In one embodiment, the subject is further administered at least one additional therapeutic agent that changes normal breathing control in the subject. In another embodiment, the additional agent is at least one selected from the group consisting of opioid narcotics, benzodiazepines, sedatives, sleeping aids, hypnotics, propofol, and any combinations thereof.

Still other embodiments relate to a method of preventing or reversing opioid (e.g., fentanyl or morphine) induced respiratory depression (OIRD) in a subject in need thereof. The method includes administering to the subject a therapeutically effective amount of a composition that includes an glutathione alkyl ester, adduct thereof, or pharmaceutically acceptable salt, tautomer, or solvate thereof.

In some embodiments, the glutathione alkyl ester can include a compound having the structure of formula:

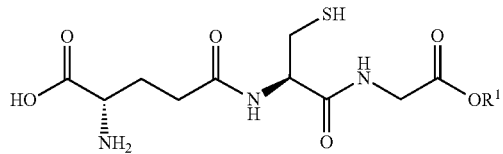

where $R^1$ is a lower alkyl ($C_1$-$C_6$ alkyl); or a pharmaceutically acceptable salt, tautomer, or solvate thereof.

In some embodiments, the glutathione alkyl ester can be an L-glutathione alkyl ester, such as an L-glutathione methyl ester or an L-glutathione ethyl ester, an adduct thereof, or a pharmaceutically acceptable salt, tautomer, or solvate thereof.

In other embodiments, the pharmaceutically acceptable salt of an glutathione alkyl ester is a hydrochloride salt.

In still other embodiment, the adduct of the glutathione alkyl ester can include at least one of an albumin adduct, a glucose adduct, an L-cysteine adduct, a D-cysteine adduct, and an S-nitroso adduct.

In some embodiments, the therapeutically effective amount of the glutathione alkyl ester, adduct thereof, or pharmaceutically acceptable salt, tautomer, or solvate thereof is an amount effective to stimulate the ventilatory and/or respiratory drive of the subject, increase tidal volume, increase respiratory frequency, increase minute ventilation, increase peak inspiratory flow, increase inspiratory drive, and/or increase Alveolar-arterial (A-a) gradient.

In other embodiments, the glutathione alkyl ester, adduct thereof, or pharmaceutically acceptable salt, tautomer, or solvate thereof is administered to the subject at an amount effective to decrease the deleterious effects of the opioid on breathing, chest-wall rigidity, ventilation-perfusion within the lungs, and arterial blood-gas chemistry without compromising the analgesic effects of the opioid in the subject.

Still other embodiments described herein relate to a composition that includes an opioid capable of inducing respiratory depression in a subject and an amount of an glutathione alkyl ester, adduct thereof, or pharmaceutically acceptable salt, tautomer, or solvate thereof effective to prevent the opioid induced respiratory depression when the composition is administered to the subject.

DETAILED DESCRIPTION

Figure 1:
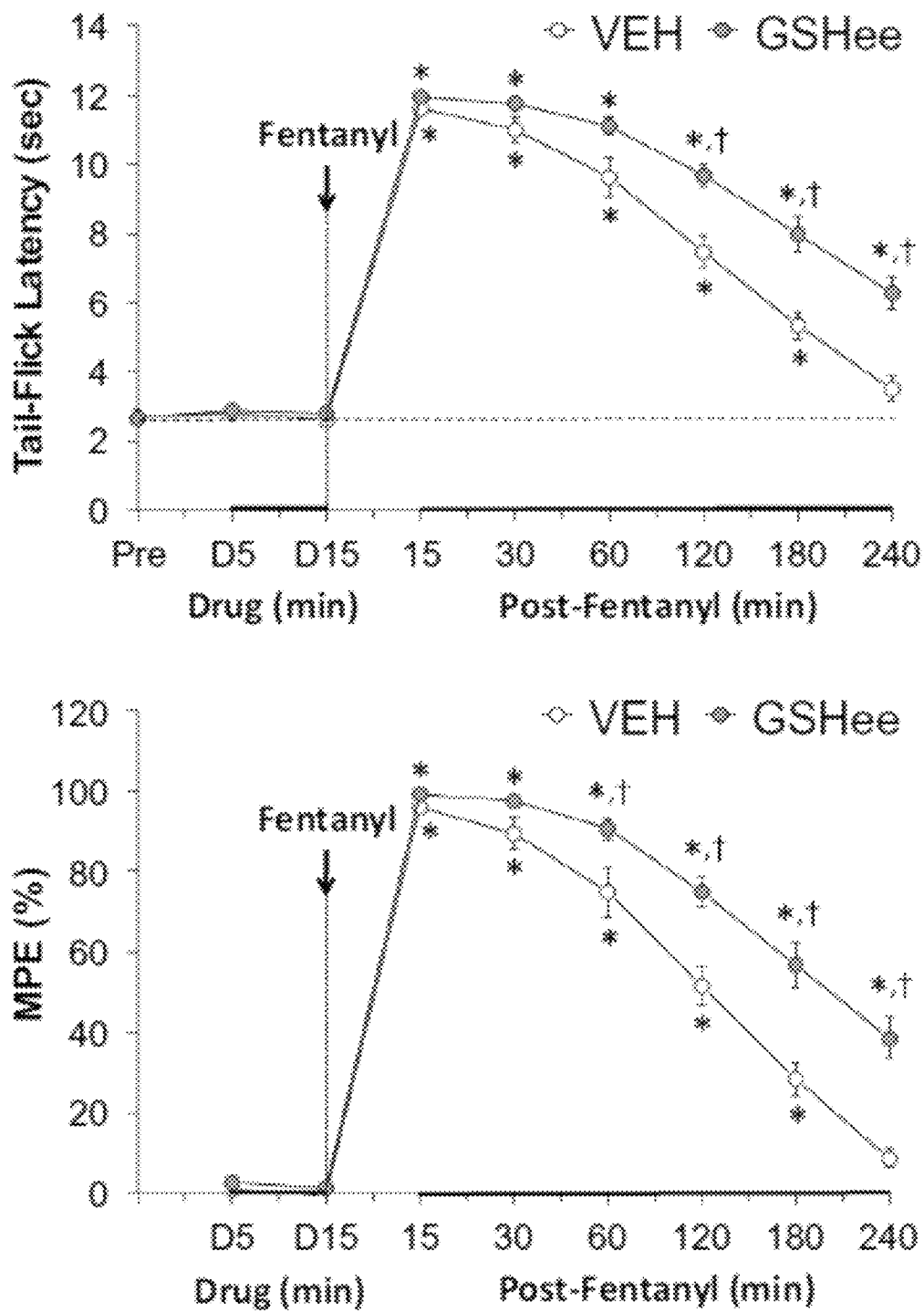
FIG. 1 illustrates: (upper panel) a plot showing the effects of fentanyl (75 μg/kg, IV) on tail-flick latencies in rats pretreated with vehicle (VEH; 1 ml/kg, IV) or GSHee (100 μmol/kg, IV). (Lower panel) a plot showing data in the upper panel expressed as maximal possible effect (MPE, %). All data are presented as mean±SEM. There were 9 rats in each group. The data were analyzed by repeated measures ANOVA followed by multiple comparison testing as detailed in the Methods section. *$P<0.05/6$ comparisons per group, significant change from post-drug (i.e., 15, 30, 60, 120, 180 or 240 min post-fentanyl versus D15 value). ′$P<0.05/6$ between group comparisons, GSHee versus vehicle.

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., Glossary of Genetics: Classical and Molecular, 5th Edition, Springer-Verlag: New York, 1991, and Lewin, Genes V, Oxford University Press: New York, 1994. The definitions provided herein are to facilitate understanding of certain terms used frequently herein and are not meant to limit the scope of the present invention.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.," as used herein are non-limiting and are for illustrative purposes only. "Including" and "including but not limited to" are used interchangeably.

The term "or" as used herein should be understood to mean "and/or", unless the context clearly indicates otherwise.

The term "about" or "approximately" as used herein refers to a quantity, level, value, number, frequency, percentage, dimension, size, amount, weight, or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight, or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight, or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore, can be produced as individual stereoisomers or as mixtures.

The term "isomerism" refers to compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substitutents, e.g., sulfoxides or sulfinimides, is likewise termed a "chiral center".

The term "chiral isomer" refers to a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n-1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric isomers" refers to diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" refers to a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The term "apnea" refers to the absence of normal breathing resulting in intermittent stoppages of breathing.

The term "Cheyne-Stokes respiration" refers to a specific pattern of breathing characterized by a crescendo pattern of breathing that results in apneas and/or hypopneas. A hallmark of this condition is that breathing becomes out of phase with blood oxygen levels.

The term "patency" refers to the state or condition of an airway being open or unblocked.

The term "hypopnea" is similar in many respects to apnea; however, breathing does not fully stop but is partially stopped (i.e., less than 100% of normal breathing, but more than 0% of normal breathing). Hypopnea is also referred to herein as "partial apnea" and can be subdivided into obstructive, central or mixed types.

The term "hypoxia" refers to a deficiency in the amount of oxygen, being taken in by an organism, as well as to a deficiency in the amount of oxygen, which is transported to tissues in an organism.

The term "normoxia" refers to a homoeostasis or "normal condition" regarding the amount of oxygen being taken in by an organism, as well as to a homeostasis or "normal condition" with respect to the amount of oxygen which is transported to tissues in an organism.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In some embodiments, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In some embodiments, the compound or active ingredient is mixed under sterile conditions with a pharmaceutically acceptable carrier, and with any preservatives, buffers, or propellants that are required.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials, which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as H2O, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

A "patient," "subject," or "host" to be treated by the compounds or methods described herein may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compounds. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament", "active ingredient", and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

All percentages and ratios used herein, unless otherwise indicated, are by weight.

Embodiments described herein relate to compositions and methods of stimulating ventilatory and/or respiratory drive in a subject in need thereof, and particularly relates to the use of a glutathione alkyl ester, adducts thereof, and/or a pharmaceutically acceptable salt, tautomer, or solvate thereof in compositions and methods of treating breathing diseases and/or disorders associated with impaired ventilator and/or respiratory drive.

In some embodiments, the methods can include stimulating ventilatory and/or respiratory drive in a subject in need thereof by administering to the subject a therapeutically effective amount of a composition that includes a glutathione alkyl ester, adduct thereof, and/or pharmaceutically acceptable salt, tautomer, or solvate thereof.

It was found that an alkyl ester form of glutathione (e.g., L-glutathione ethyl ester (GSHee)) is a potent stimulant of ventilatory and/or respiratory drive that effectively overcome breathing disorders and that an alkyl ester form of glutathione can effectively prevent the ventilatory depressant effects of opioids, such as opioid-induced respiratory depression (OIRD), and their deleterious effects on breathing stability and gas-exchange within the lungs without compromising, impairing, attenuating, and/or adversely affecting narcotic-induced the analgesic action of the opioid. In addition, it was found that glutathione (GSH) itself can have positive effects on breathing but did not attenuate the negative effects of an opioid on breathing parameters. Without being bound by theory, it is believed that an alkyl ester of glutathione can enhance the central processes driving the end of expiration (inspiratory on-switch) and thus decrease expiratory duration and that the thiolester moiety may directly inhibit the ability of an opioid to suppress the central processes driving expiration under opioid-induced hypoxic/hypercapnic conditions and/or the direct inhibitory effects of an opioid on expiratory muscle activity.

In some embodiments, the glutathione alkyl esters, adducts thereof, and pharmaceutically acceptable salts, tautomers, or solvates thereof can be administered to a subject in need thereof at an amount or therapeutically effective amount to stimulate the ventilatory and/or respiratory drive of the subject, including, for example, increasing tidal volume, increasing respiratory frequency, increasing minute ventilation, increasing peak inspiratory flow, increasing inspiratory drive, and/or increasing Alveolar-arterial (A-a) gradient.

In some embodiments, the glutathione alkyl ester can include a compound having the structure of formula:

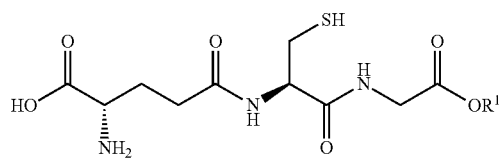

where $R^1$ is a lower alkyl ($C_1$-$C_6$ alkyl); or a pharmaceutically acceptable salt, tautomer, or solvate thereof. In other embodiments, $R^1$ is selected from the group consisting of methyl, ethyl, propyl, and butyl.

In some embodiments, the glutathione alkyl ester can be an L-glutathione alkyl ester, such as an L-glutathione methyl ester or an L-glutathione ethyl ester, an adduct thereof, or a pharmaceutically acceptable salt, tautomer, or solvate thereof.

In still other embodiment, the adduct of the glutathione alkyl ester can be a biologically active adduct and include at least one of an albumin adduct, a glucose adduct, an L-cysteine adduct, an D-cysteine adduct, or an S-nitroso adduct.

Composition comprising an glutathione alkyl ester, adduct thereof, and/or pharmaceutically acceptable salt, tautomer, or solvate thereof described herein can be administered to a subject to stimulate ventilatory and/or respiratory drive in a subject in need thereof. In some embodiments, the subject can have or is at increased risk of impaired ventilatory and/or respiratory drive associated with a disorder or breathing disorder, such as respiratory depression, including narcotic, sedative, and/or anesthetic, induced suppression of respiratory drive or ventilatory drive, sleep apnea (central, mixed and obstructive including but not limited to co-existing conditions of heart failure, kidney disease and stroke), sleep-disordered breathing (especially with snoring and arousals), apnea of prematurity, allergies, neurological or neuromuscular diseases (e.g., stroke or amyotrophic lateral sclerosis (ALS)), weakened respiratory muscles, hypoventilation due to stroke, trauma, surgery and/or radiation, obesity-hypoventilation syndrome, primary alveolar hypoventilation syndrome, acquired central hypoventilation syndromes (ACHS), congenital central hypoventilation syndromes (CCHS), chronic bronchitis, Cheyne-Stokes respiration, dyspnea, altitude sickness or acclimatization to high altitude, hypopnea, hypoxia, hypercapnia, cystic fibrosis, chronic obstructive pulmonary disease (COPD), nasal septum deformation, tonsillitis, adenoiditis, and Arnold-Chiari syndrome. The composition can be administered to the subject at an amount effective to treat and/or prevent the breathing disorder or impaired ventilatory and/or respiratory drive associated with the disorder or breathing disorder.

In some embodiments, the composition can be administered to the subject to prevent the need for mechanical ventilation in subjects with acutely impaired ventilatory and/or respiratory drive because of an acute exacerbation of an underlying lung disease or an acute requirement for narcotic analgesia. For example, the subjects can be at-risk subjects with severe, hypercapneic COPD or mixed apnea evident on polysomnography.

In other embodiments, the subject can have or has an increased risk of respiratory depression or suppressed ventilatory drive that is caused, for example, by an anesthetic, a sedative, anxiolytic agent, a hypnotic agent, alcohol, and/or a narcotic. By way of a non-limiting example, narcotic analgesics (e.g., morphine, fentanyl, oxycodone, buprenorphine) are administered to cancer patients to alleviate pain. The dose is often limited by a fear of respiratory depression. In addition, even a partial respiratory depression from these drugs causes hypoxia and a resulting excessive daytime sleepiness that can be debilitating and severely decrease quality of life. General anesthetics can exert a similar depressant effect on respiration and delay a patient's transfer from the operating room to a surgical recovery area. A composition comprising an glutathione alkyl ester, adduct thereof, or pharmaceutically acceptable salt, tautomer, or solvate thereof described herein is therefore useful to counteract the lingering effects of the anesthetic, and for restoring adequate respiratory drive to enable the patient to breathe on their own.

In certain embodiments, a therapeutically effective amount of the glutathione alkyl ester, adduct thereof, or pharmaceutically acceptable salt, tautomer, or solvate thereof can be administered to a subject in need thereof to prevent or reverse opioid (e.g., fentanyl or morphine) induced respiratory depression in a subject in need thereof. The therapeutically effective amount of the glutathione alkyl ester, adduct thereof, or pharmaceutically acceptable salt, tautomer, or solvate thereof is an amount effective to stimulate the ventilatory and/or respiratory drive of the subject, increase tidal volume, increase respiratory frequency, increase minute ventilation, increase peak inspiratory flow, increase inspiratory drive, and/or increase Alveolar-arterial (A-a) gradient.

In other embodiments, the glutathione alkyl ester, adduct thereof, or pharmaceutically acceptable salt, tautomer, or solvate thereof is administered to the subject at an amount effective to decreases the deleterious effects of the opioid on breathing, chest-wall rigidity, ventilation-perfusion within the lungs, and arterial blood-gas chemistry without compromising the analgesic effects of the opioid in the subject.

In other embodiments, a composition including the glutathione alkyl ester, adduct thereof, or pharmaceutically acceptable salt, tautomer, or solvate thereof can be administered in ambulatory delivery formulations to treat respiratory depression associated with narcotics, analgesics, sedatives, and/or opioids. The subject can be one who is taking and/or over-dosed on the narcotics, analgesics, sedatives, and/or opioids and who is experiencing or at risk of acute respiratory depression. The compositions can be administered to the subject to treat stimulate ventilatory and/or respiratory drive and increase breathing frequency.

In some embodiments, a subject can include a subject with an increased risk of decreased respiratory drive such as a subject with a significant chronic obstructive pulmonary disease or cor pulmonale, and those with a substantially decreased respiratory reserve, hypoxia, hypercapnia, or preexisting respiratory depression. Elderly, cachectic, or debilitated subjects may have altered pharmacokinetics or altered opioid clearance compared to younger, healthier patients resulting in greater risk for respiratory depression.

In some embodiments, compositions comprising the glutathione alkyl ester, adduct thereof, or pharmaceutically acceptable salt, tautomer, or solvate thereof described herein can be administered to the subject in combination with at least one additional compound, agent, and/or therapeutic agent useful for treating the subject or the breathing disorder. These additional compounds, agents, and/or therapeutic agents can include commercially available agents or compounds, known to treat, prevent, or reduce the symptoms of breathing disorders or treat the disorder in the subject.

In some embodiments, the at least one additional therapeutic agent can change normal breathing in a subject. Such additional agents can be selected from the group consisting of an opioid, doxapram and enantiomers thereof, acetazolamide, almitrine, GAL021, theophylline, caffeine, methylprogesterone and related compounds, sedatives that decrease arousal threshold in sleep disordered breathing patients, sodium oxybate, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, and combinations thereof.

In some embodiments, the at least one additional therapeutic agent is a non-opioid receptor (OR) ventilatory stimulant that does not affect opioid-induced analgesia. Such additional agents can be selected from the group consisting of Dl-dopamine receptor agonists (e.g., apomorphine, pergolide, rotigotine, terguride, clozapine, fenoldopam, adrogolide, and dihydrexidine and derivatives thereof), ampakines (e.g., CX-516 (Ampalex), CX-546, CX-614, CX-691 (farampator), and CX-717 and ORG-26576), thyrotropin-releasing hormone (TRH), glycyl-glutamine (gly-gln), and phosphodiesterase-4 inhibitors (e.g., apremilast, crisaboroie, cilomilast, and roflurnilast).

In other embodiments, compositions comprising the glutathione alkyl ester, adduct thereof, or pharmaceutically acceptable salt, tautomer, or solvate thereof described herein and at least one additional compound has additive, complementary or synergistic effects in the treatment of the breathing disorder or other disorder in the subject. In a non-limiting example, the compositions that include the glutathione alkyl ester, adduct thereof, or pharmaceutically acceptable salt, tautomer, or solvate thereof described herein may be used concurrently or in combination with one or more of the following drugs: an opioid (e.g., morphine, oxycodone, fentanyl), doxapram, enantiomers of doxapram, acetazolamide, almitrine, GAL021, theophylline, caffeine, methylprogesterone and related compounds, sedatives that decrease arousal threshold in sleep disordered breathing patients (e.g., eszopiclone and zolpidem), sodium oxybate, benzodiazepine receptor agonists (e.g., zolpidem, zaleplon, eszopiclone, estazolam, flurazepam, quazepam, temazepam, triazolam), orexin antagonists (e.g., suvorexant), tricyclic antidepressants (e.g., doxepin), serotonergic modulators, adenosine and adenosine receptor and nucleoside transporter modulators, cannabinoids (e.g., but not limited to, dronabinol), orexins, melatonin agonists (e.g., ramelteon) and compounds known as ampakines.

The combination of two or more compounds may refer to a composition wherein the individual compounds are physically mixed or wherein the individual compounds are physically separated. A combination therapy encompasses administering the components separately to produce the desired additive, complementary or synergistic effects.

In one embodiment, the composition comprising the glutathione alkyl ester, adduct thereof, or pharmaceutically acceptable salt, tautomer, or solvate thereof described herein and an additional agent are physically mixed in the composition. In another embodiment, the composition comprising the glutathione alkyl ester, adduct thereof, or pharmaceutically acceptable salt, tautomer, or solvate thereof described herein and the additional agent are physically separated in the composition.

In one embodiment, compositions comprising the glutathione alkyl ester, adduct thereof, or pharmaceutically acceptable salt, tautomer, or solvate thereof described herein is co-administered with a compound that is used to treat another disorder but causes loss of breathing control. In this aspect, compositions comprising the glutathione alkyl ester, adduct thereof, or pharmaceutically acceptable salt, tautomer, or solvate thereof described herein block or otherwise reduce depressive effects on normal breathing control caused by the compound with which they are co-administered. An exemplary compound that treats another disorder but depresses breathing control includes but is not limited to anesthetics, sedatives, sleeping aids, anxiolytics, hypnotics, alcohol, and narcotic analgesics. The co-administered compound may be administered individually, or a combined composition as a mixture of solids and/or liquids in a solid, gel or liquid formulation or as a solution, according to methods known to those familiar with the art.

In some embodiments, a composition comprising the glutathione alkyl ester, adduct thereof, or pharmaceutically acceptable salt, tautomer, or solvate thereof described herein may be packaged with at least one additional compound useful for treating breathing control disorders. In another embodiment, a composition comprising an glutathione alkyl ester described herein may be packaged with a therapeutic agent known to cause changes in breathing control, such as, but not limited to, anesthetics, sedatives, anxiolytics, hypnotics, alcohol, and narcotic analgesics. A co-package may be based upon, but not limited to, dosage units. For example, a composition can include an opioid capable of inducing respiratory depression in a subject and an amount of an glutathione alkyl ester, adduct thereof, or pharmaceutically acceptable salt, tautomer, or solvate thereof effective to prevent the opioid induced respiratory depression when the composition is administered to the subject.

In other embodiment, a glutathione alkyl ester, adduct thereof, or pharmaceutically acceptable salt, tautomer, or solvate thereof can be administered in combination albumin and/or as an albumin adduct. It has been shown that thiol ester compounds can complex with albumin upon administration to a subject and that the complexing albumin can enhance the therapeutic effect of the thiol ester in a subject in need thereof. Therefore, in some embodiments, albumin can be administered to the subject in combination with a glutathione alkyl ester compound described herein to increase the therapeutic efficacy of the glutathione alkyl ester in the subject.

In some embodiments, a subject administered a combination of albumin and an glutathione alkyl ester is a hypoalbuminemic subject. To indentify a hypoalbuminemic subject, the subject's serum albumin level can be measured using well known laboratory methods. For example, albumin is generally measured in a subject by a dye-binding technique that utilizes the ability of albumin to form a stable complex with bromocresol green dye (BCG). The serum albumin level can be measured in the plasma, serum, urine or other biological fluid samples obtained from a subject. The normal serum protein level in a human subject is about 6 to about 8 g/dl. In some embodiments, a subject having below 3.5 grams per deciliter of serum albumin is considered to have hypoalbuminemia.

In some embodiments, in addition to a combination of albumin and the glutathione alkyl ester, a subject may be administered one or more agents or medications capable of raising the albumin level in the subject. In alternative embodiments, a subject is administered a combination of one or more agents capable of raising the albumin level in the subject and an glutathione alkyl ester described herein. In certain embodiment, especially where the subject has a kidney condition, an agent capable of raising the albumin level in the subject (e.g., a hypoalbuminemic subject) can include a blood pressure medication employed to prevent a subject from passing albumin out though urine. Exemplary blood pressure medications for use in a method described herein can include but are not limited to captopril and benazepril.

Additional agents capable of raising the albumin level in a subject include immunosuppressive agents to reduce inflammation related albumin loss in the subject. For example, in some embodiments, immunosuppressant agents, such as a corticosteroid, can be administered to a subject in addition to a combination of albumin and the glutathione alkyl ester. Alternatively, an immunosuppressant agent can be administered to a subject in place of albumin in combination with a glutathione alkyl ester.

The glutathione alkyl ester, adduct thereof, or pharmaceutically acceptable salt, tautomer, or solvate thereof and/or additional compounds or agents described herein can be provided in a pharmaceutical composition with a pharmaceutically acceptable carrier or excipient. In some embodiment, pharmaceutical compositions that include the glutathione alkyl ester, adduct thereof, or pharmaceutically acceptable salt, tautomer, or solvate thereof described herein may be formulated to deliver a dose to the subject of between 1 ng/kg/day and 100 mg/kg/day. In another embodiment, the pharmaceutical compositions may be administered to deliver a dose of glutathione alkyl ester, adduct thereof, or pharmaceutically acceptable salt, tautomer, or solvate thereof between 1 ng/kg/day and 500 mg/kg/day.

The relative amounts of the glutathione alkyl ester, adduct thereof, or pharmaceutically acceptable salt, tautomer, or solvate thereof, the pharmaceutically acceptable carrier, and any additional ingredients in a pharmaceutical composition can vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods described herein may be suitably developed for nasal, inhalational, oral, rectal, vaginal, pleural, peritoneal, parenteral, topical, transdermal, pulmonary, intranasal, buccal, ophthalmic, epidural, intrathecal, intravenous or another route of administration. Other contemplated formulations include projected nanoparticles, microspheres, liposomal preparations, coated particles, and polymer conjugates.

In one embodiment, compositions that include the glutathione alkyl ester, adduct thereof, or pharmaceutically acceptable salt, tautomer, or solvate thereof described herein are part of a pharmaceutical matrix, which allows for manipulation of insoluble materials and improvement of the bioavailability thereof, development of controlled or sustained release products, and generation of homogeneous compositions. By way of example, a pharmaceutical matrix may be prepared using hot melt extrusion, solid solutions, solid dispersions, size reduction technologies, molecular complexes (e.g., cyclodextrins, and others), microparticulate, and particle and formulation coating processes. Amorphous or crystalline phases may be used in such processes.

The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

Although the descriptions of pharmaceutical compositions provided herein are principally directed to pharmaceutical compositions, which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions is contemplated include, but are not limited to, humans and other primates, mammals including commercially relevant mammals such as cattle, pigs, horses, sheep, cats, and dogs.

In one embodiment, the compositions described herein are formulated using one or more pharmaceutically acceptable excipients or carriers. Pharmaceutically acceptable carriers, which are useful, include, but are not limited to, glycerol, water, saline, ethanol, recombinant human albumin, solubilized gelatins, and other pharmaceutically acceptable salt solutions, such as phosphates and salts of organic acids. Examples of these and other pharmaceutically acceptable carriers are described in Remington's Pharmaceutical Sciences (1991, Mack Publication Co., New Jersey).

In some embodiments, the carrier may be a solvent or dispersion medium containing, for example, water, ethanol, polyol (for example, glycerol, propylene glycol, and liquid polyethylene glycol, and the like), recombinant human albumin, solubilized gelatins, suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

Formulations of the compositions described herein may be employed in admixtures with conventional excipients, i.e., pharmaceutically acceptable organic or inorganic carrier substances suitable for oral, parenteral, nasal, inhalational, intravenous, subcutaneous, transdermal enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or fragrance-conferring substances and the like. They may also be combined where desired with other active agents, e.g., other analgesic, anxiolytics or hypnotic agents. As used herein, "additional ingredients" include, but are not limited to, one or more ingredients that may be used as a pharmaceutical carrier.

The composition may comprise a preservative from about 0.005% to 2.0% by total weight of the composition. The preservative is used to prevent spoilage in the case of exposure to contaminants in the environment. Examples of preservatives include but are not limited to those selected from the group consisting of benzyl alcohol, sorbic acid, parabens, imidurea and combinations thereof. A particular preservative is a combination of about 0.5% to 2.0% benzyl alcohol and 0.05% to 0.5% sorbic acid.

The composition can include an antioxidant and a chelating agent which inhibit the degradation of the compound. Examples of antioxidants for some compounds are BHT, BHA, alpha-tocopherol and ascorbic acid in the range of about 0.01% to 0.3% by weight by total weight of the composition. The chelating agent can be present in an amount of from 0.01% to 0.5% by weight by total weight of the composition. Examples of chelating agents include edetate salts (e.g., disodium edetate) and citric acid in the weight range of about 0.01% to 0.20% by weight by total weight of the composition. The chelating agent is useful for chelating metal ions in the composition, which may be detrimental to the shelf life of the formulation.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, acacia, and ionic or non-ionic surfactants. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin.

Liquid solutions of the active ingredient in aqueous or oily solvents may be prepared in substantially the same manner as liquid suspensions, the primary difference being that the active ingredient is dissolved, rather than suspended in the solvent. An "oily" liquid is one which comprises a carbon-containing liquid molecule and which exhibits a less polar character than water. Liquid solutions of the pharmaceutical composition may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, ionic and non-ionic surfactants, and a preservative. Additional excipients, such as fillers and sweetening, flavoring, or coloring agents, may also be included in these formulations.

A pharmaceutical composition may also be prepared, packaged, or sold in the form of oil-in-water emulsion or a water-in-oil emulsion. The oily phase may be a vegetable oil, such as olive or *arachis* oil, a mineral oil, such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying. Methods for mixing components include physical milling, the use of pellets in solid and suspension formulations and mixing in a transdermal patch, as known to those skilled in the art.

The regimen of administration may affect what constitutes an effective amount. The therapeutic formulations may be administered to the patient either prior to or after the onset of a breathing disorder event or ventilator depressant effects of the opioid. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the glutathione alkyl ester, adduct thereof, or pharmaceutically acceptable salt, tautomer, or solvate thereof described herein to a patient, preferably a mammal, more preferably a human, may be carried out using known procedures, at dosages and for periods of time effective to modulate breathing control and/or respiratory and ventilatory drive in the patient. An effective amount of the therapeutic compound sufficient to achieve a therapeutic effect may vary according to factors, such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for the glutathione alkyl ester, adduct thereof, or pharmaceutically acceptable salt, tautomer, or solvate thereof is from about 0.01 mg/kg to 100 mg/kg of body weight/per day. One of ordinary skill in the art would be able to study the relevant factors and make the determination regarding the effective amount of the therapeutic compound without undue experimentation.

The compositions that include the glutathione alkyl ester, adduct thereof, or pharmaceutically acceptable salt, tautomer, or solvate thereof described herein may be administered to an animal, such as a human, as frequently as several times daily, or it may be administered less frequently, such as once a day, once a week, once every two weeks, once a month, or even less frequently, such as once every several months or even once a year or less. It is understood that the amount of composition or glutathione alkyl ester, adduct thereof, or pharmaceutically acceptable salt, tautomer, or solvate thereof described herein dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds employed in the pharmaceutical composition at levels lower than that required in order to achieve the desired therapeutic effect and gradually increase the dosage until the desired effect is achieved.

Other embodiments described herein relate to a method of treating a subject in need thereof, such as a subject without normal ventilation and/or normal breathing control, by administering the compositions comprising the glutathione alkyl ester, adduct thereof, or pharmaceutically acceptable salt, tautomer, or solvate thereof described herein, and additionally treating the patient using a device to support breathing. Such devices include, but are not limited to, ventilation devices, CPAP and BiPAP devices.

Mechanical ventilation is a method to mechanically assist or replace spontaneous breathing. Mechanical ventilation is typically used after an invasive intubation, a procedure wherein an endotracheal or tracheostomy tube is inserted into the airway. It is normally used in acute settings, such as in the ICU, for a short period of time during a serious illness. It may also be used at home or in a nursing or rehabilitation institution, if patients have chronic illnesses that require long-term ventilation assistance. The main form of mechanical ventilation is positive pressure ventilation, which works by increasing the pressure in the patient's airway and thus forcing air into the lungs. Less common today are negative pressure ventilators (for example, the "iron lung") that create a negative pressure environment around the patient's chest, thus sucking air into the lungs. Types of mechanical ventilation are: conventional positive pressure ventilation, high frequency ventilation, non-invasive ventilation (non-invasive positive pressure ventilation or NIPPV), proportional assist ventilation (PAY), adaptive servo ventilation (ASV) and neurally adjusted ventilatory assist (NAVA).

Non-invasive ventilation refers to all modalities that assist ventilation without the use of an endotracheal tube. Non-invasive ventilation is primarily aimed at minimizing patient discomfort and the complications associated with invasive ventilation, and is often used in cardiac disease, exacerbations of chronic pulmonary disease, sleep apnea, and neuromuscular diseases. Non-invasive ventilation refers only to the patient interface and not the mode of ventilation used; modes may include spontaneous or control modes and may be either pressure or volume cycled modes.

Some commonly used modes of NIPPV include continuous positive airway pressure (CPAP). This kind of machine has been used mainly by patients for the treatment of sleep apnea at home, but now is in widespread use across intensive care units as a form of ventilatory support. The CPAP machine stops upper airway obstruction by delivering a stream of compressed air via a hose to a nasal pillow, nose mask or full-face mask, splinting the airway open (keeping it open under air pressure) so that unobstructed breathing becomes possible, reducing and/or preventing apneas and hypopneas. When the machine is turned on, but prior to the mask being placed on the head, a flow of air comes through the mask. After the mask is placed on the head, it is sealed to the face and the air stops flowing. At this point, it is only the air pressure that accomplishes the desired result. This has the additional benefit of reducing or eliminating the extremely loud snoring that sometimes accompanies sleep apnea.

Bi-level positive airway pressure (BIPAP) alternate between inspiratory positive airway pressure (IPAP) and a lower expiratory positive airway pressure (EPAP), triggered by patient effort. On many such devices, backup rates may be set, which deliver IPAP pressures even if patients fail to initiate a breath.

The invention is further illustrated by the following example, which is not intended to limit the scope of the claims.

EXAMPLE

In this Example we determined: (1) the effects of (L-glu-thathione ethyl ester (GSHee)) on ventilatory performance in freely-moving adult rats; and (2) whether the prior administration of GSHee is able to ameliorate the negative effects of fentanyl on breathing and gas-exchange in freely-moving adult rats. The results demonstrate that GSHee (100 µmol/kg, IV) has pronounced positive effects on breathing in freely-moving adult male Sprague—Dawley rats and that it markedly attenuates the deleterious effects elicited by subsequent injection of fentanyl (75 µg/kg, IV) on minute ventilation, A-a gradient and ABG chemistry while extending the analgesic actions of the OR agonist. In contrast, the injection of GSH itself (100 µmol/kg, IV), while having positive effects on breathing did not attenuate the negative effects of this dose of fentanyl on breathing parameters.

Methods

Rats and Surgical Procedures

All studies were carried out in accordance with the NIH Guide for the Care and Use of Laboratory Animals (NIH Publication No. 80-23) revised in 1996. In addition, all studies were carried out in compliance with the ARRIVE (Animal Research: Reporting of In Vivo Experiments) guidelines. The protocols were approved by the Animal Care and Use Com-mittees of the University of Virginia and Case Western Reserve University. Adult male Sprague—Dawley rats (Harlan, Madison, WI, USA) were implanted with jugular vein catheters under 2% isoflurane anesthesia and some rats received femoral arterial catheters. The rats were allowed at least four days to recover from surgery before use. All arterial catheters were flushed daily with heparin solution (50 units heparin in phosphate-buffered saline at 0.1 M, pH 7.4). All catheters were flushed with phosphate-buffered saline (0.1 M, pH 7.4) approximately four hours before commencement of the experiments. All studies were performed in a quiet laboratory with relative humidity of 50±2% and room temperature of 21.3±0.2° C.

Antinociception Protocols

Antinociception was determined by a radiant heat tail-flick (TF) assay. The intensity of the light was adjusted so that baseline TF latencies were approximately 3 s. A cutoff time of 12 s was set to minimize damage to the tail. Baseline TF latencies were established and after 15 min, the rats were injected with vehicle (saline, 1 ml/kg, IV; n=9 rats; 316±2 g) or GSHee (100 µmol/kg, IV; n=9; 317±2 g) and TF latencies were then recorded after 5 and 15 min. At that point, all of the rats received an injection of fentanyl (75 m/kg, IV) and TF latencies were recorded at 15, 30, 60, 120, 180 and 240 min thereafter. The data are shown as actual TF latencies (sec) and as "maximum possible effect" (% MPE) using the formula, % MPE=[(post-injection TF latency—baseline TF latency)/(12— baseline TF latency)]×100.

Protocols for Blood Gas Measurements and Determination of Arterial-Alveolar Gradient Arterial blood samples (100 µL) were taken 15 min before, 1, 7.5 and 15 min after injection of vehicle (saline, IV; n=9 rats; 322±2 g) or GSHee (100 µmol/kg, IV; n=9 rats; 320±2 g) and 1, 5, 10, 15 and 20 min after injection of fentanyl (75 m/kg, IV). The pH, $pCO_2$, $pO_2$ and $sO_2$ of the samples were measured using a Radiometer blood-gas analyzer (ABL800 FLEX). A-a gradient measures the difference between alveolar and arterial blood $O_2$ concentrations. A decrease in $PaO_2$, without a change in A-a gradient is caused by hypo-ventilation whereas a decrease in $PaO_2$ with an increase in A-a gradient indicates ventilation—perfusion mismatch. A-a gradient=$PAO_2$— $PaO_2$, where $PAO_2$ is the partial pressure of alveolar 02 and $PaO_2$ is $pO_2$ in arterial blood. $PAO_2$=$[(FiO_2 \times (P_{atm} - P_{H2O})) - (PaCO_2/\text{respiratory quotient})]$, where $FiO_2$ is the fraction of $O_2$ in inspired air; $P_{atm}$ is atmospheric pressure; $P_{H2O}$ is the partial pressure of H2O in inspired air; $PaCO_2$ is $pCO_2$ in arterial blood; and respiratory quotient (RQ) is the ratio of $CO_2$ eliminated/02 consumed. We took $FiO_2$ of room-air to be 21%=0.21, $P_{atm}$ to be 760 mmHg, and $P_{H2O}$ to be 47 mmHg. We took the RQ value of our adult male rats to be 0.9.

Body Temperature (BT) Protocols

Changes in BT impact the size of recorded flow-related variables in plethysmography chambers. Our chambers do not monitor BT, but it is imperative to record BT to under-stand its influence on GSHee on fentanyl-induced changes in ventilation. Adult male Sprague—Dawley rats were placed in separate open plastic boxes and allowed 60-90 min to acclimatize. BT was recorded as described previously. A thermistor probe, inserted 5-6 cm into the rectum to allow regular recording of BT, was connected to a telethermometer (Yellow Springs Instruments) was taped to the tail. BT was recorded every 5 min during acclimatization to establish baseline values. One group of rats received vehicle (saline, 1 ml/kg, IV; n=9 rats; 321±2 g) and another received GSHee (100 µmol/kg, IV; n=9 rats; 318±2 g) and BT was recorded at 5 and 15 min post-injection. Both groups then received an injection of fentanyl (75 µg/kg, IV) and BT was recorded 5, 10, 15, 20, 25 and 30 min later.

Whole-Body Plethysmography Measurement of Ventilatory Parameters

Ventilatory parameters were recorded in freely-moving rats by whole body plethysmography (PLY3223; Data Sciences International, St. Paul, MN) as described previously. The rats were allowed 60 min to acclimatize to the chambers and to allow true resting ventilatory parameters to be established. One group of rats received vehicle (saline, 1 ml/kg, IV; n=9 rats; 326±2 g) and another received GSHee (100 µmol/kg, IV; n=9 rats; 329±2 g). After 15 min, all rats received an injection of fentanyl (75 µg/kg, IV). The effects of bolus injections of GSH (100 µmol/kg, IV; 324±3 g; n=9 rats) or vehicle (saline; 326±2 g; n=9 rats) on fr, Vt and Ve were determined in freely-moving male Sprague—Dawley rats and the subsequent effects of fentanyl (75 µg/kg, IV) given 15 min were also determined in both groups of rats. Due to the closeness of the body weights of the two groups of rats, ventilatory data are shown without body weight corrections. Parameters were breathing frequency (fr), tidal volume (Vt), minute ventilation (Ve), inspiratory time (Ti), expiratory time (Te), peak inspiratory (PIF) and peak expiratory (PIF) flows. The provided software (Fine Pointe, BUXCO) constantly corrected digitized values for changes in chamber temperature and humidity. Pressure changes associated with the respiratory waveforms were then converted to volumes (i.e., Vt, PIF and PEF) using the algorithm of Epstein and colleagues. Specifically, factoring in chamber temperature and humidity, the cycle analyzers filtered the acquired signals, and BUXCO algorithms (Fine Pointe) generated an array of box flow data that identified a waveform segment as an acceptable breath. From that data vector, the minimum and maximum values were determined. Flows at this point were considered to be "box flow" signals. From this array, the minimum and maximum box flow values were determined and multiplied by a compensation factor provided by the selected algorithm, thus producing Vt, PIF and PEF values that were used to determine accepted and rejected waveforms reported as Rejection Index (non-eupneic breathing). All directly recorded parameters including Rejection Index (see below) were extracted from the raw waveforms using Data Sciences International (St. Paul, MN, USA) proprietary Biosystem XA software (version 2.9.0.2) and proprietary FinePointe software (version v2.8.0), as described previously and as detailed in the Data Sciences International/Buxco website reference to the list of parameters provided by FinePointe Soft-ware using whole body plethysmography (https://www.datasci.com/products/buxco-respiratory-products/finep ointe-whole-body-plethysmography). The BioSystem XA software extracts the waveforms that are analyzed by the FinePointe software that uses National Instruments Measurement Studio to perform these analyses (http://zone.ni.com/reference/en-XX/help/372636F-01/mstudiowebhelp/htm1/5d5b3031/).

Righting Reflex

Separate groups of adult male Sprague—Dawley rats were used to evaluate the effects of GSHee (100 µmol/kg, IV) on the duration of fentanyl (75 µg/kg, IV)-induced impairment of the righting reflex (inability to stand on all four legs). Each rat was placed in an open plastic chamber to allow the duration of the loss of righting reflex to be accurately recorded. The time at which the rat spontaneously stood on all four paws was taken as the point of recovery. In this study, one group of rats (320±2 g, n=12) received an injection of vehicle (saline) and after 15 min, an injection of fentanyl. A second group of rats (323±2 g, n=12) received an injection of GSHee and after 15 min an injection of fentanyl. The duration of effect of fentanyl was defined as the time interval from the time of injection of fentanyl administration to the recovery of righting reflex.

Statistics

The recorded data (1 min bins) and derived parameters, Vt/Ti and Response Area (cumulative percent changes from pre-values) were taken for statistical analyses. The pre-drug 1 min bins excluded occasional marked deviations from resting due to movements or scratching by the rats. These exclusions ensured accurate determinations of baseline parameters. The data are presented as mean±SEM. All data were analyzed by one-way or two-way analysis of variance followed by Student's modified t test with Bonferroni corrections for multiple comparisons between means using the modified error mean square term (EMS) from the ANOVA. The modified t-statistic is t=(mean group 1—mean group 2)/[s x $(1/n_1+1/n_2)1/2$] where s2=the mean square within groups term from the ANOVA (the square root of this value is taken for the modified t-statistic formula) and $n_1$ and $n_2$ are the number of rats in each group. Based on an elementary inequality called Bonferroni's inequality, a conservative critical value for the modified t-statistics is obtained from tables of t-distribution using a significance level of P/m, where m is the number of comparisons between groups to be performed. The degrees of freedom are those for the mean square for within group variation from the ANOVA table. In most cases, the critical Bonferroni value cannot be obtained from conventional tables of the t-distribution but may be approximated from widely available tables of the normal curve by $t^*=z+(z+z3)/4n$, where n is the degrees of freedom and z is the critical normal curve value for P/m. As demonstrated by Wallenstein et al. the Bonferroni procedure is recommended for general use since it is easiest to apply, has the widest range of applications, and gives critical values that will be lower than those of other procedures if the investigator is able to limit the number of comparisons, and that will be only slightly larger than those of other procedures if many comparisons are made. A value of $P<0.05$ was taken as the initial level of statistical significance.

Results

Tail-Flick Latencies

As summarized in FIG. 1, a bolus injection of GSHee (100 µmol/kg, IV) or vehicle (VEH, IV) did not alter TFL as measured 5 and 15 min after administration. The subsequent injection of fentanyl (75 µg/kg, IV) elicited robust antinociception for at least 180 min in vehicle-treated rats. As also seen in FIG. 1, the duration of the fentanyl-induced antinociception was greater in GSHee-pretreated rats than in the vehicle-pretreated rats.

Arterial Blood-Gas Chemistry and A-a Gradient

Figure 2:
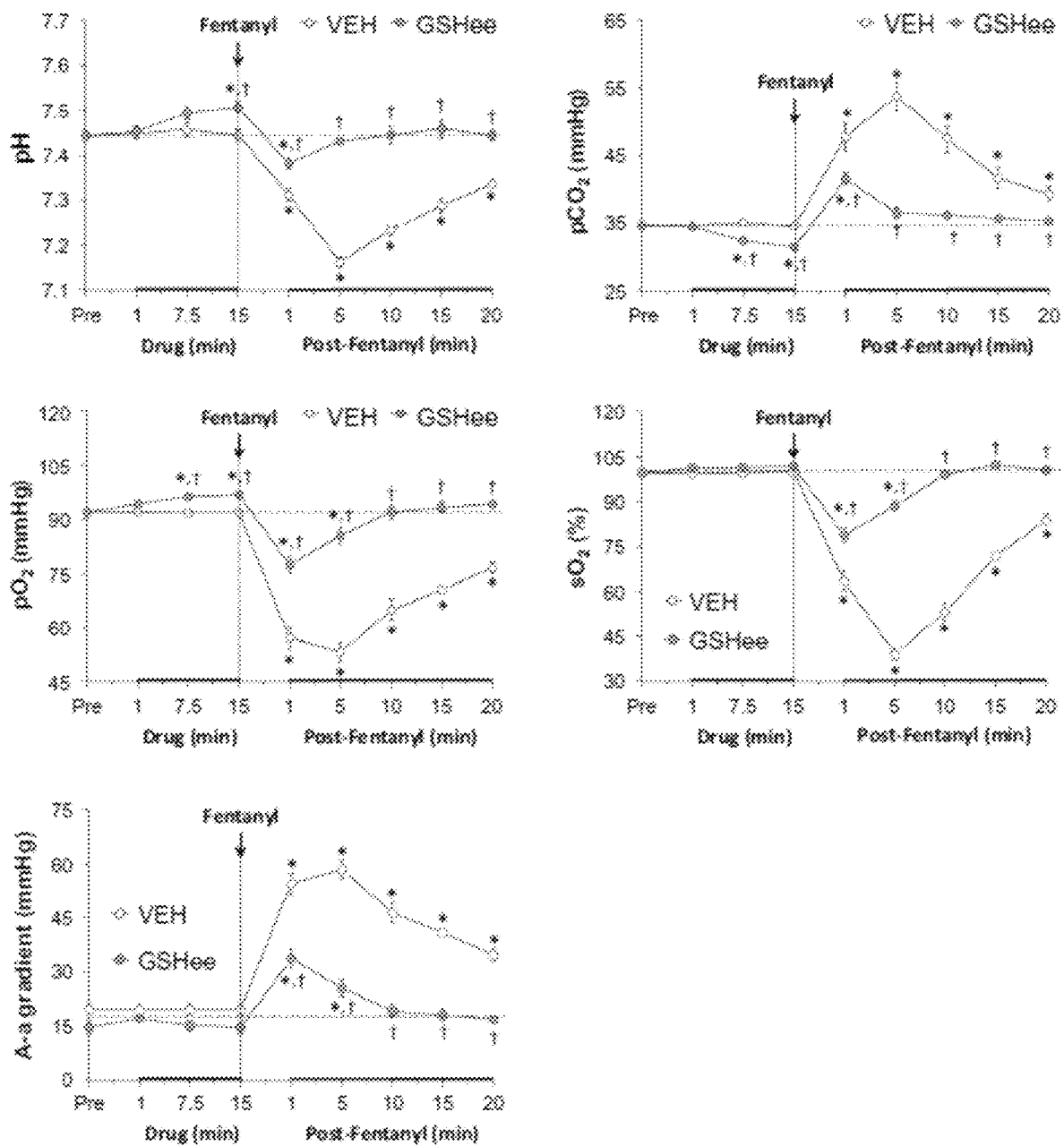
FIG. 2 illustrates plots showing the effects of fentanyl (75 μg/kg, IV) on arterial blood pH, $pO_2$, $pCO_2$ and $sO_2$ values and Alveolar-arterial (A-a) gradients in rats pretreated with vehicle (VEH; 1 ml/kg, IV) or GSHee (100 μmol/kg, IV). The data are presented as mean±SEM. The data were analyzed by repeated measures ANOVA followed by multiple comparison testing as detailed in the Methods section. There were 9 rats in each group. *$P<0.05/5$ comparisons per group, significant change from post-drug. ′$P<0.05/5$ between group comparisons, GSHee versus vehicle.

As summarized in FIG. 2, the injection of GSHee (100 µmol/kg, IV) elicited minor but significant increases in pH and $pO_2$ that were accompanied by a minor but significant decrease in $pCO_2$. These responses were still evident 20 min after injection of fentanyl. GSHee did not affect $sO_2$ or A-a gradient. The injection of fentanyl (75 µg/kg, IV) in vehicle-treated rats elicited dramatic decreases in arterial blood pH, $pO_2$ and $sO_2$ that were accompanied by substantial increases in $pCO_2$ and A-a gradient (FIG. 2). The changes in ABG chemistry and A-a gradient were markedly smaller in magnitude and of substantially shorter duration in the GSHee-pretreated rats.

Body Temperature

The changes in BT elicited by injection of fentanyl (75 µg/kg, IV) in vehicle-treated or GSHee (100 µmol/kg, IV)-treated rats were determined. Prior to the injections, both groups had similar resting BT values. Neither vehicle nor GSHee affected BT as recorded at 5 and 15 min post-injection. The injection of fentanyl in vehicle-treated rats elicited a small but significant hyperthermia. Fentanyl elicited a similar minor hyperthermia in the GSHee-treated rats.

Ventilatory Parameters

Figure 3:
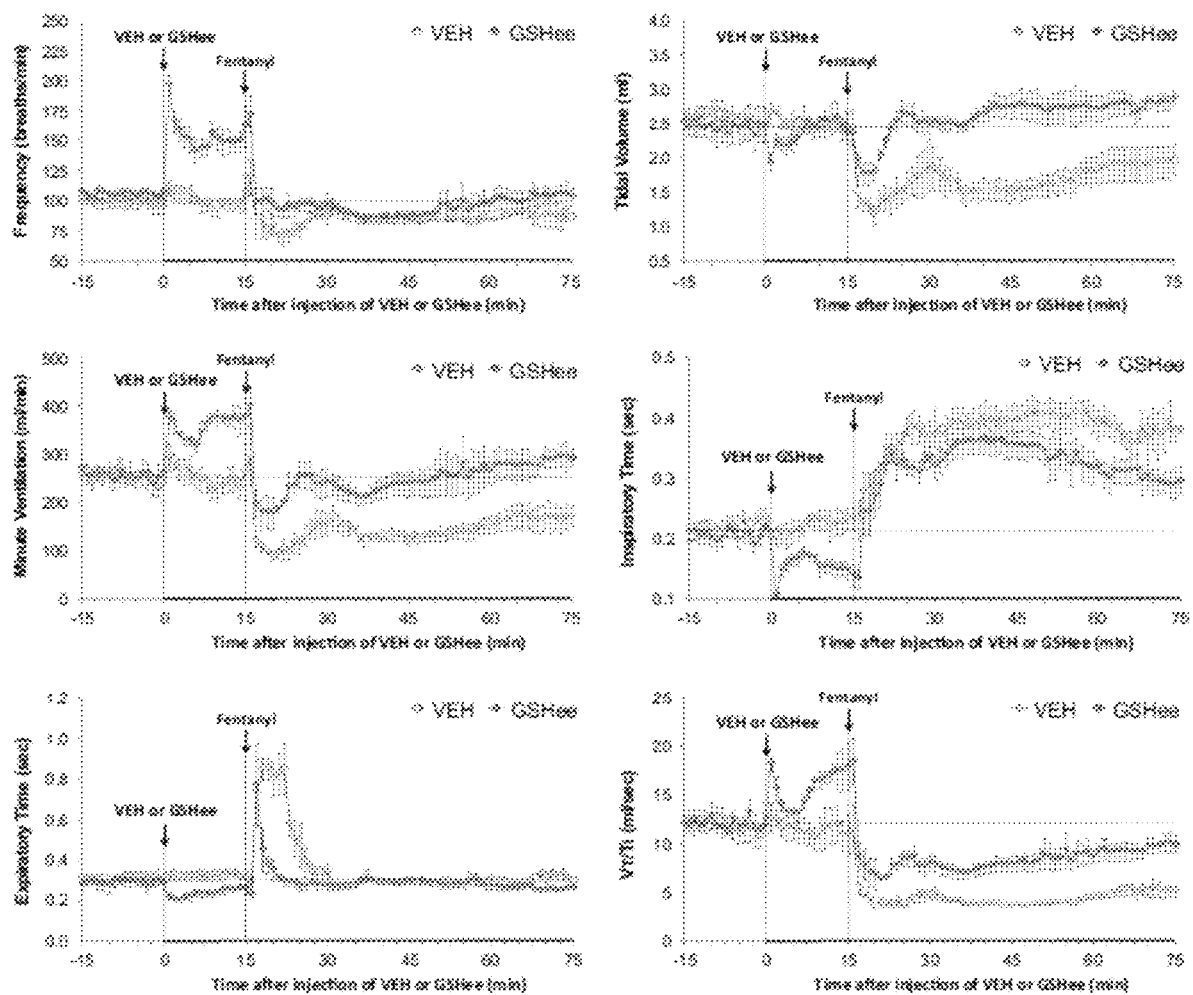
FIG. 3 illustrates plots showing the effects of fentanyl (75 μg/kg, IV) on frequency of breathing (top left panel), tidal volume (top right panel), inspiratory time (middle left panel), minute ventilation (middle right panel), expiratory time (bottom left panel) and tidal volume/inspiratory time (Vt/Ti) in rats pretreated with vehicle (VEH; 1 ml/kg, IV) or GSHee (100 μmol/kg, IV). The data are presented as mean±SEM. There were 9 rats in each group. The stippled horizontal line denotes average resting values before injection of GSHee or vehicle.

As summarized in FIG. 3, the injection of GSHee elicited a prompt and sustained increase in breathing frequency (fr) that was accompanied by expected decreases in inspiratory time (Ti) and expiratory time (Te). GSHee did not affect tidal volume (Vt) and so the sustained increase in minute ventilation (Ve) was due entirely to the increase in fr. The changes in Vt and Ti resulted in a biphasic increase in inspiratory drive (Vt/Ti). The injection of vehicle did not alter any of the above ventilatory parameters. Subsequent injection of fentanyl in vehicle-treated rats elicited (a) a decrease in fr associated with a pronounced and sustained increase in Ti and a pronounced but shorter in duration increase in Te, and (b) sustained decreases in Vt, Ve and inspiratory drive (Vt/Ti). Subsequent injection of fentanyl in GSHee-treated rats elicited (i) a substantially smaller decrease in fr that was accompanied by a substantially smaller increase in Te but a smaller reduction of the increase in Ti, and (ii) smaller decreases in Vt, Ve and inspiratory drive.

Figure 4:
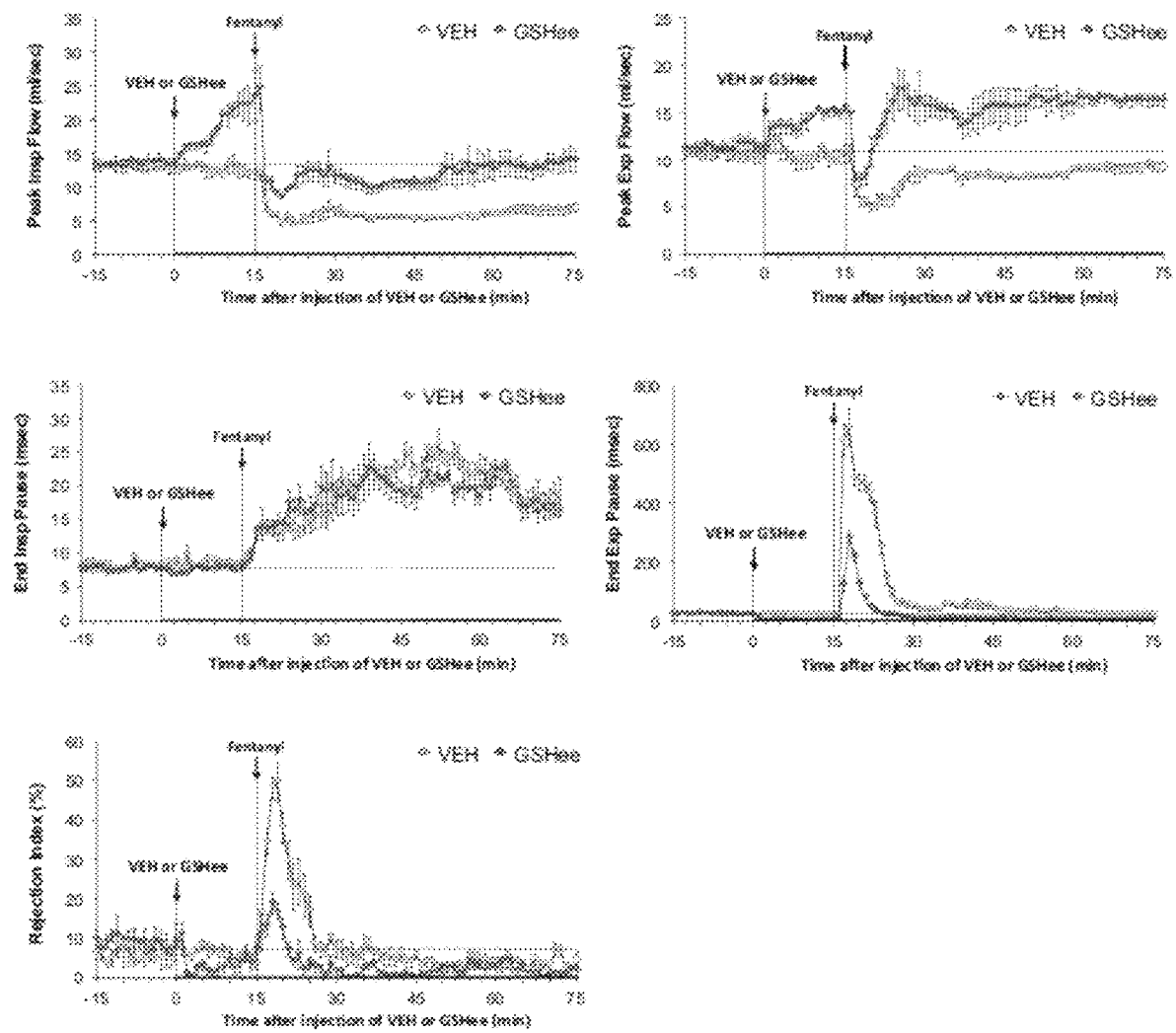
FIG. 4 illustrates plots showing the effects of fentanyl (75 μg/kg, IV) on peak inspiratory flow (top left panel), peak expiratory flow (top right panel), end inspiratory pause (middle left panel), end expiratory pause (middle right panel), and Rejection Index (bottom left panel) in rats pretreated with vehicle (VEH; 1 ml/kg, IV) or GSHee (100 μmol/kg, IV). The data are presented as mean±SEM. There were 9 rats in each group. The stippled horizontal line denotes average resting values before injection of GSHee or vehicle.

As shown in the top panels of FIG. 4, GSHee elicited robust increases in peak inspiratory flow (PIF) and peak expiratory flow (PEF) that were still present at the time fentanyl was injected 15 min later. Fentanyl elicited pronounced and sustained decreases in PIF and PEF in the vehicle-treated rats. The injection of fentanyl elicited a robust and sustained decrease in PIF in the GSHee-treated rats but the levels of PIF did not fall markedly below baseline (pre-GSHee levels). In contrast, fentanyl elicited a transient reduction in PEF with the levels quickly returning and remaining at the elevated levels elicited by GSHee. As shown in the middle panels of FIG. 4, GSHee elicited robust decreases in end expiratory pause (EEP), but only minor changes in end inspiratory pause (EIP) (more readily seen in FIG. 5). The subsequent injection of fentanyl elicited pronounced and sustained increases in EIP that were similar in the vehicle- and GSHee-treated rats. In contrast, fentanyl elicited a marked increase in EEP for approximately 25 min in the vehicle-treated rats, but a markedly smaller response of lesser duration in the GSHee-treated rats. Finally, the bottom panel of FIG. 4 shows that GSHee elicited a fall in Rejection Index (Rinx, decrease in non-eupneic breathing) that had transpired by the time fentanyl was given. The subsequent injection of fentanyl elicited a marked increase in Rejection Index for approximately 15 min in vehicle-treated rats, but a markedly smaller increase of lesser duration in GSHee-treated rats. Rejection Index tended to drop in both groups of fentanyl-injected rats, most noticeably about 30 min after injection of fentanyl (45 min after injection of vehicle or GSHee).

Figure 5:
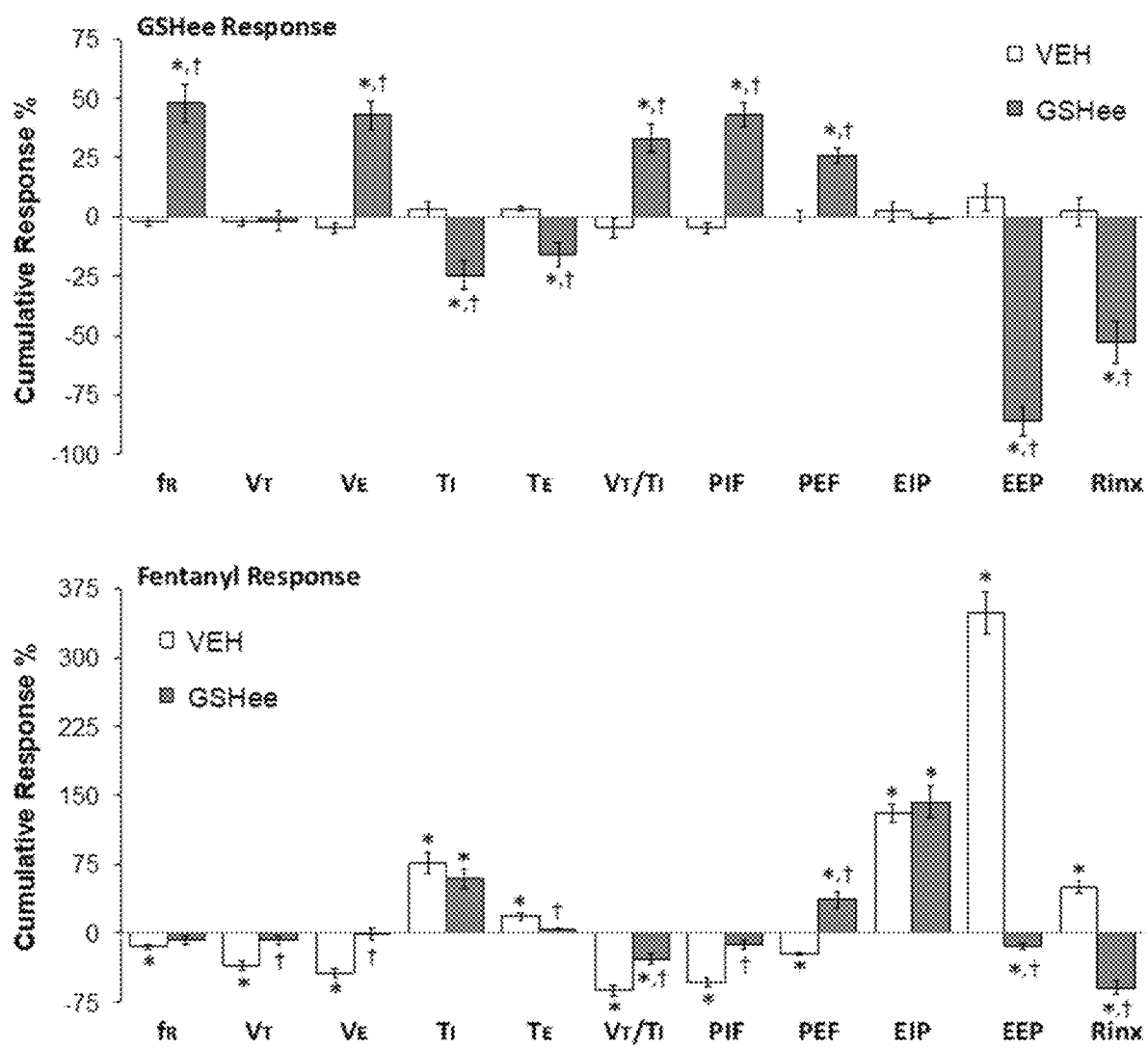
FIG. 5 illustrates graphs showing the cumulative ventilatory responses elicited by the injections of vehicle, fentanyl in vehicle, or GSHee. Top Panel: Cumulative ventilatory responses (expressed as % change from pre-values) elicited by the injections of vehicle (VEH; 1 ml/kg, IV) or GSHee (100 μmol/kg, IV) recorded over the 15 min period immediately prior to injection of fentanyl. The 15 values were added together to obtain the cumulative response for each rat and the mean and SEM of these values from the 9 rats was calculated. Bottom panel: Cumulative ventilatory responses (expressed as % change from pre-values) elicited by the injections of fentanyl (75 μg/kg, IV) in vehicle- or GSHee (100 μmol/kg, IV)-treated rats recorded over the 60 min period following injection of fentanyl. There were 9 rats in each group. *$P<0.025$, significant response. ′$P<0.025$, GSHee versus vehicle. Please note that the ANOVA plus multiple comparisons tests were done for each independent variable separately. As such, for Frequency of breathing for example, the ANOVA (and subsequent multiple comparisons testing) was constructed to analyze whether (a) the vehicle or GSHee responses were significant and whether the GSHee responses were different from the vehicle responses, and (b) whether the fentanyl responses were significant in the vehicle-treated or GSHee-treated rats and whether the fentanyl induced responses in the GSHee-treated rats were different from those in the vehicle-treated rats. Accordingly, for each variable there were 2 between-group comparisons and the modified P values was set at $0.05/2=0.025$.
Figure 6:
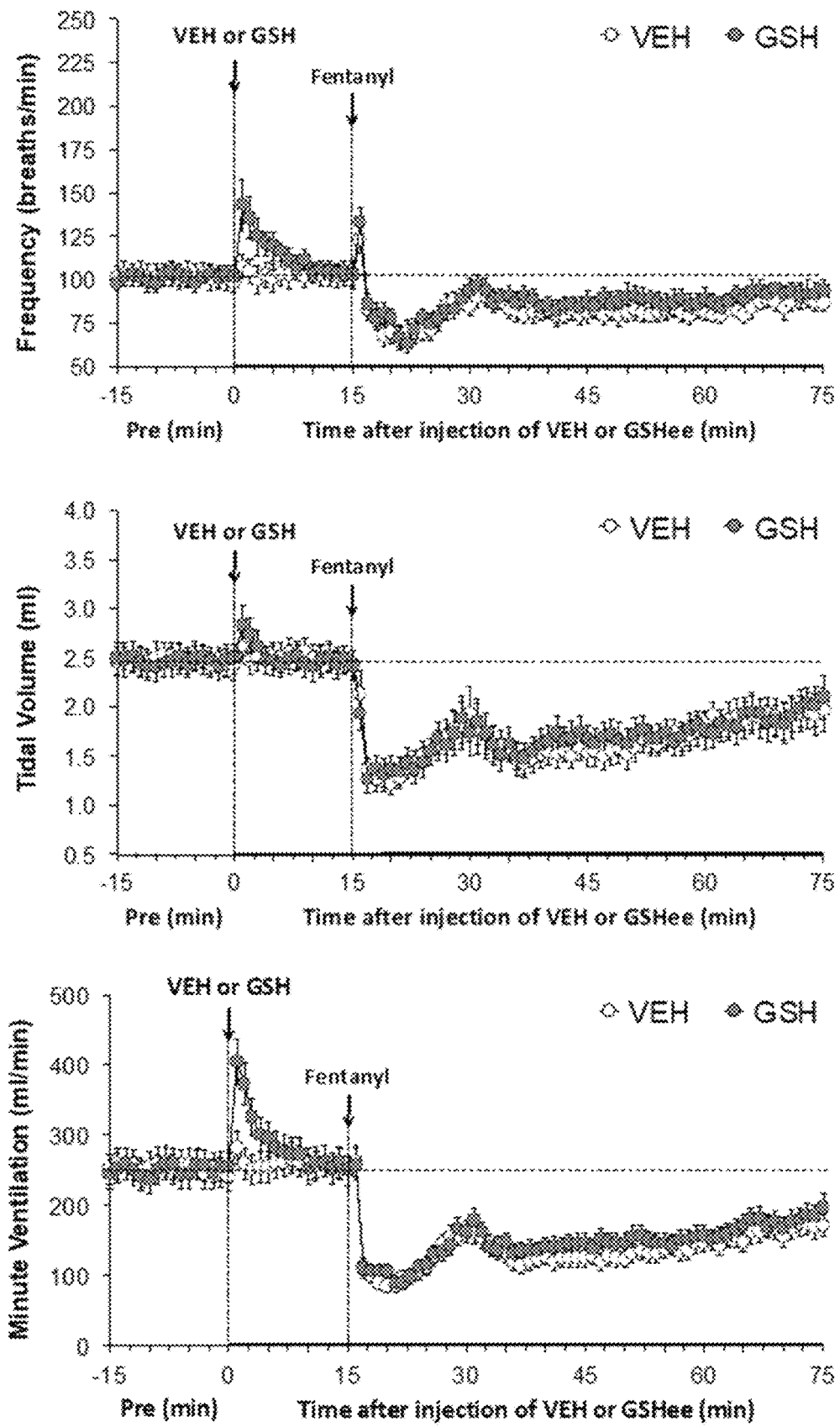
FIG. 6 illustrates plots showing the effects of fentanyl (75 μg/kg, IV) on frequency of breathing (top panel), tidal volume (middle panel) and minute ventilation (bottom panel), in rats pretreated with vehicle (VEH; 1 ml/kg, IV) or glutathione (GSH, 100 μmol/kg, IV). The data are presented as mean±SEM. There were 9 rats in each group. The stippled horizontal line denotes average resting values before injection of GSHee or vehicle.

FIG. 5 summarizes the cumulative responses elicited by injections of vehicle (VEH) or GSHee (top panel) recorded over the 15 min-period prior to injection of fentanyl and those elicited by subsequent injection of fentanyl recorded for 60 min (bottom panel). The injection of vehicle did not elicit cumulative changes in any ventilatory parameter. GSHee elicited cumulative increases in Ve, which was due solely to increases in fr not Vt. GSHee elicited cumulative decreases in Ti and Te; cumulative increases in inspiratory drive (Vt/Ti), PIF, and PEF; no cumulative change in EIP, but cumulative decreases in EEP and Rejection Index. The subsequent injection of fentanyl in the vehicle-treated rats (bottom panel) elicited cumulative decreases in fr, Vt and Ve; cumulative increases in Ti and to a lesser extent Te; cumulative decreases in PIF and PEF; and cumulative increases in EIP, EEP and Rejection Index. Pretreatment with GSHee prevented/attenuated/reversed the fentanyl-induced cumulative decreases in Vt, Ve, Vt/Ti, PIF, PEF, and fentanyl-induced cumulative increases in EIP, EEP and Rejection Index. We also investigated whether pre-treatment with GSH (100 µmol/kg, IV) itself would modulate the ventilatory depressant effects of fentanyl (75 µg/kg, IV). The baseline (Pre) fr, Vt and Ve values in the two groups of rats used in this study are presented in Table 1. There were no-between group differences in any parameter. The changes in fr, Vt and Ve elicited by the injection of vehicle (VEH, saline) or GSH and the subsequent responses elicited by fentanyl are summarized in FIG. 6. As can be seen, the injection of GSH elicited a prompt but short-lived increase in Freq with minor effects on TV that resulted in short-lived increases in MV. The responses elicited by the subsequent injection of fentanyl were similar in the vehicle- or GSH-treated rats.

TABLE 1

| Phase | Frequency (breaths/min) | | Tidal Volume (ml) | | Minute Ventilation (ml/min) | |
|---|---|---|---|---|---|---|
| | Vehicle | GSH | Vehicle | GSH | Vehicle | GSH |
| Pre (baseline) values | 102 ± 7 | 101 ± 5 | 2.48 ± 0.14 | 2.46 ± 0.15 | 254 ± 22 | 251 ± 19 |
| Peak drug response, % | +5 ± 4 | +41 ± 7*,† | +4 ± 3 | +15 ± 4*,† | +11 ± 7 | 61 ± 8*,† |
| Total drug response, % | +1 ± 3 | +13 ± 3*,† | +1 ± 3 | +2 ± 3 | +2 ± 4 | 15 ± 3*,† |

TABLE 1-continued

| | Frequency (breaths/min) | | Tidal Volume (ml) | | Minute Ventilation (ml/min) | |
|---|---|---|---|---|---|---|
| Phase | Vehicle | GSH | Vehicle | GSH | Vehicle | GSH |
| Fentanyl-peak decrease, % | −35 ± 6* | −38 ± 5* | −51 ± 7* | −49 ± 6* | −66 ± 9* | −64 ± 8* |
| Fentanyl-total decrease, % | −19 ± 3* | −14 ± 3* | −33 ± 4* | −31 ± 5* | −46 ± 7* | −40 ± 6* |

GSH, glutathione.
The peak drug (vehicle or GSH at 100 μmol/kg, IV) and fentanyl (75 μg/kg, IV) responses are expressed as % change from Pre-values.
The total changes elicited by drug (vehicle, GSH) or fentanyl represent the sum of the 15 individual % change from pre values.
The data are presented as mean ± SEM.
There were 9 rats in each group.
*$P < 0.05$ comparisons, sigificant change from Pre-values.
†$P < 0.05/3$ comparisons, GSH versus Vehicle.

GSH, glutathione. The peak drug (vehicle or GSH at 100 μmol/kg, IV) and fentanyl (75 μg/kg, IV) responses are expressed as % change from Pre-values. The total changes elicited by drug (vehicle, GSH) or fentanyl represent the sum of the 15 individual % change from pre values. The data are presented as mean±SEM. There were 9 rats in each group. *$P<0.05$ comparisons, significant change from Pre-values. ′$P<0.05/3$ comparisons, GSH versus Vehicle.

TABLE 2

Effects of fentanyl (75 μg/kg, IV) on body temperature in vehicle-or GSHee (100 μmol/kg, IV)-treated conscious rats

| | Time | Treatment Groups | |
|---|---|---|---|
| Phase | (min) | Vehicle | GSHee |
| Pre | 30 | 37.8 ± 0.1 | 37.7 ± 0.1 |
| | 15 | 37.9 ± 0.1 | 37.8 ± 0.1 |
| | 5 | 37.8 ± 0.1 | 37.8 ± 0.1 |
| | Average | 37.8 ± 0.1 | 37.8 ± 0.1 |
| Post-drug | 5 | 37.8 ± 0.1 | 37.9 ± 0.1 |
| | 15 | 37.9 ± 0.1 | 37.9 ± 0.1 |
| Post-fentanyl | 5 | 37.8 ± 0.1 | 37.9 ± 0.1 |
| | 10 | 38.0 ± 0.1 | 38.0 ± 0.1 |
| | 15 | 38.0 ± 0.1 | 38.0 ± 0.1 |
| | 20 | 38.1 ± 0.1 | 38.2 ± 0.1 |
| | 25 | 38.2 ± 0.1 | 38.2 ± 0.1 |
| | 30 | 38.1 ± 0.1 | 38.2 ± 0.1 |
| Change from Pre (° C.) | 5 | −0.02 ± 0.10 | 0.06 ± 0.09 |
| | 10 | 0.13 ± 0.09 | 0.17 ± 0.11 |
| | 15 | 0.09 ± 0.08 | 0.13 ± 0.10 |
| | 20 | 0.21 ± 0.08* | 0.31 ± 0.09* |
| | 25 | 0.29 ± 0.05* | 0.33 ± 0.10* |
| | 30 | 0.23 ± 0.08* | 0.31 ± 0.08* |

The data are presented as mean ± SEM.
There were 9 rats in each group.
*$P < 0.05$, significant change from Pre.
There were no between-group differences in the effects of fentanyl ($P > 0.05/6$ comparaisons at 5, 10, 15, 20, 25, 30 min, for all between-group comparisions).

The data are presented as mean±SEM. There were 9 rats in each group. *$P<0.05$, significant change from Pre. There were no between-group differences in the effects of fentanyl ($P>0.05/6$ comparisons at 5, 10, 15, 20, 25 and 30 min, for all between-group comparisons).

TABLE 3

Baseline respiratory values prior to administration of any drugs

| Parameter | Vehicle | GSHee |
|---|---|---|
| Number of rats | 9 | 9 |
| Frequency, breaths/min | 98 ± 5 | 104 ± 5 |
| Tidal volume, ml | 2.56 ± 0.12 | 2.44 ± 0.20 |
| Minute Ventilation, ml/min | 249 ± 15 | 254 ± 18 |
| Inspiratory Time, sec | 0.218 ± 0.013 | 0.206 ± 0.015 |
| Expiratory Time, sec | 0.311 ± 0.021 | 0.285 ± 0.023 |
| Tidal Volume/Respiratory Time, ml/sec | 12.0 ± 1.0 | 11.9 ± 0.6 |
| End Inspiratory Pause, msec | 8.3 ± 0.3 | 7.7 ± 0.4 |
| End Expiratory Pause, msec | 22.1 ± 1.7 | 24.1 ± 0.8 |
| Peak Inspiratory Flow, ml/sec | 13.2 ± 0.7 | 13.4 ± 0.8 |
| Peak Expiratory Flow, ml/sec | 10.6 ± 0.4 | 11.3 ± 0.5 |
| Rejection Index (%) | 6.5 ± 0.9 | 8.8 ± 1.8 |

The data are presented as mean ± SEM.
There were 9 rats in each group.
There were no between-group differences for any resting parameter ($P > 0.05$, for all comparisons).

The data are presented as mean±SEM. There were 9 rats in each group. There were no between-group differences for any resting parameter ($P>0.05$, for all comparisons).

TABLE 4

Baseline ventilatory parameters and vehicle, glutathione (GSH) and fentanyl-induced responses

| | Frequency (breaths/min) | | Tidal Volume (ml) | | Minute Ventilation (ml/min) | |
|---|---|---|---|---|---|---|
| Phase | Vehicle | GSH | Vehicle | GSH | Vehicle | GSH |
| Pre (baseline) values | 102 ± 7 | 101 ± 5 | 2.48 ± 0.14 | 2.46 ± 0.15 | 254 ± 22 | 251 ± 19 |
| Peak drug response, % | +5 ± 4 | +41 ± 7*,† | +4 ± 3 | +15 ± 4*,† | +11 ± 7 | 61 ± 8*,† |

TABLE 4-continued

Baseline ventilatory parameters and vehicle, glutathione (GSH) and fentanyl-induced responses

| Phase | Frequency (breaths/min) | | Tidal Volume (ml) | | Minute Ventilation (ml/min) | |
|---|---|---|---|---|---|---|
| | Vehicle | GSH | Vehicle | GSH | Vehicle | GSH |
| Total drug response, % | +1 ± 3 | +13 ± 3*,† | +1 ± 3 | +2 ± 3 | +2 ± 4 | 15 ± 3*,† |
| Fentanyl-peak decrease, % | −35 ± 6* | −38 ± 5* | −51 ± 7* | −49 ± 6* | −66 ± 9* | −64 ± 8* |
| Fentanyl-total decrease, % | −19 ± 3* | −14 ± 3* | −33 ± 4* | −31 ± 5* | −46 ± 7* | −40 ± 6* |

GSH, glutathione.
The peak drug (vehicle or GSH at 100 μmol/kg, IV) and fentanyl (75 μg/kg, IV) responses are expressed as % change from Pre-values.
The total changes elicited by drug (vehicle, GSH) or fentanyl represent the sum of the 15 individual % change from pre values.
The data are presented as mean ± SEM.
There were 9 rats in each group.
*$P < 0.05$ comparisons, sigificant change from Pre-values.
†$P < 0.05/3$ comparisons, GSH versus Vehicle.

GSH, glutathione. The peak drug (vehicle or GSH at 100 μmol/kg, IV) and fentanyl (75 μg/kg, IV) responses are expressed as % change from Pre-values. The total changes elicited by drug (vehicle, GSH) or fentanyl represent the sum of the 15 individual % change from pre values. The data are presented as mean±SEM. There were 9 rats in each group. *P<0.05 comparisons, significant change from Pre-values. tP<0.05/3 comparisons, GSH versus Vehicle.

TABLE 5 changes in inspiratory and expiratory times and their ratio at three time of the study

| | Actual Values | | | % Change from Pre | |
|---|---|---|---|---|---|
| Parameter | Pre | +5 min | +30 min | +5 min | +30 min |
| $T_I$, sec | 0.22 ± 0.01 | 0.35 ± 0.03* | 0.38 ± 0.03* | +61 ± 7* | +74 ± 8* |
| $T_E$, sec | 0.32 ± 0.02 | 0.81 ± 0.09* | 0.31 ± 0.03 | +152 ± 16* | −4 ± 6 |
| $T_I/T_E$ | 0.68 ± 0.03 | 0.43 ± 0.04* | 1.23 ± 0.15* | −37 ± 5* | +81 ± 9* |

$T_I$, inspiratory time; $T_E$, expiratory time; The data are presented as mean ± SEM.
There were 9 rats in each group.
*$P < 0.05/2$ comparisons, significant change for +5 min and/or +30 min values from Pre-values for each parameter.
†$P < 0.05/3$ comparisions, +30 min versus +5 min values for the 3 parameters.

T1, inspiratory time; TE, expiratory time; The data are presented as mean±SEM. There were 9 rats in each group. *P<0.05/2 comparisons, significant change for +5 min and/or +30 min values from Pre-values for each parameter. 'P<0.05/3 comparisons, +30 min versus +5 min values for the 3 parameters.

Behaviors

Despite the relatively pronounced increase in Freq in the rats that received GSHee, the rats that did not display any obvious behavioral signs (e.g., movement, squealing, scratching or sniffing) and the rats that were lying quietly at the time of injection, remained so immediately during and following the injection. In addition, the duration of the pronounced sedation elicited by fentanyl was very similar in vehicle- or GSHee-treated rats. More specifically, we determined that in other groups of adult male Sprague—Dawley rats that injection of fentanyl (75 μg/kg, IV) caused immediate sedation (the rats quickly become immobile and lay on their side with eyes most often closed). The full return of the righting-reflex in vehicle-treated rats (43±6 min, n=12) and GSHee (100 μmol/kg, IV)-treated rats (54±9 min, n=12) were similar to one another (P>0.05, GSHee versus vehicle).

The intravenous injection of 100 μmol/kg (33.54 mg/kg) of GSHee elicited an array of responses in freely-moving adult male Sprague—Dawley rats and had dramatic effects on the responses elicited by subsequent injection of fentanyl (100 μmol/kg). It is likely that GSHee exerts its effects in naïve rats by increasing levels of GSH and metabolites (γ-glutamylcysteinyl and cysteine) in cells (e.g., neurons) in which GSH and the metabolites affect a number of biological processes. It is unlikely that GSHee directly inhibits OR function (loss of affinity or down-regulation of membrane accessible receptors) since GSHee augmented the analgesic effects of fentanyl, which are known to be OR-mediated. It is well known that morphine can markedly lower GSH and cysteine levels in brain and peripheral tissues. The finding that the injection of GSH itself did not blunt the ventilatory depressant effects of fentanyl raises the tentative suggestion that the bioactivity of GSHee may be due to the enhanced ability of the thiolester to enter cells that control breathing and that this intracellular entry is related to the sustained efficacy of GSHee against some of the actions of fentanyl.

With respect to analgesia, GSHee did not elicit observable changes in analgesia status of freely moving rats per se whereas the duration of fentanyl analgesia was increased in rats pretreated with the thiolester. The mechanisms by which GSHee augments fentanyl-induced analgesia are probably multi-factorial and likely to involve modulation of analgesia-signaling pathways within the periphery, spinal cord and brain. Indeed, it may be possible that GSHee modulates opioid receptor signaling processes that result in fentanyl becoming a "biased" ligand so that the opioid receptor signaling pathways now favor analgesia rather than respiratory depression. Whatever the mechanism, opioid-induced analgesia augmentation is a very important attribute for an OIRD drug candidate. The dose of fentanyl we chose for this study (75 μg/kg, IV) elicited a robust decrease in minute ventilation (approximately 50% over a period of at least 60 min) and so represents a substantial level of ventilatory impairment by which to examine the effects of the 100 μmol/kg dose of GSHee.

The ability of GSHee to affect ventilatory parameters in naïve rats was as complex as it was impressive. First, GSHee elicited a sustained increase in Ve via the sustained increase in fr that was accompanied by the expected decreases in both Ti and Te, whereas it had minimal effects on Vt. It would seem likely that GSHee drives fr by actions within the carotid bodies by mechanisms including direct effects on neurotransmitter release from primary *glomus* cells. It remains possible that nitrosyl derivatives of GSHee such as S-nitrosoglutathione and S-nitrosocysteinylglycine or S-nitrosocysteine drive an increase in fr by activating carotid body *glomus* cells, chemoafferent terminals in the carotid bodies, or by actions in brain sites such as the nucleus tractus solitarius, a key nucleus of ventilatory processing. Despite minimal effects on Vt (actual volume of air taken in each breath), GSHee did elicit a sustained increase in both PIF and PEF, which suggests the thiolester either directly affected the force of contraction of skeletal muscle in the extrinsic (inspiratory) and intrinsic (expiratory) intercostals and/or diaphragm. This would be consistent with considerable in vitro evidence that GSH enhances both $Ca^{2+}$-dependent and $Ca^{2+}$-independent skeletal muscle contractility.

The mechanisms by which fentanyl exerts its longer-lasting effects on Ti remain to be determined. The effects on GSHee on the fentanyl-induced changes in Te (GSHee dramatically curtailed the effects of fentanyl on Te) were perhaps more remarkable than they were on Ti (GSHee somewhat diminished the magnitude rather than the duration of the longer lasting elevation in Ti). We cannot speculate on how GSHee elicits these effects but it is clear that it is available to interfere with the processes by which fentanyl suppresses active and passive phases of breathing. Fentanyl would be expected to cause non-eupneic breathing with more variation in phase length as the respiratory rate drops. Indeed, we found that the relative increases in Ti and Te were substantially different during the peak decreases in fr elicited by fentanyl (approximately +5 min post-injection, see FIG. 3). As can be seen in Table 5, Te lengthened considerably more than Ti at the +5 min time-point such that the Ti/Te ratio fell dramatically (−37±5%). Moreover, at the 30 min post-fentanyl time-point when fr was close to return to pre-values (see FIG. 3), Ti was still substantially longer than pre-fentanyl whereas Te had returned to pre-values so that the Ti/Te ratio rose dramatically (+81±9%). As also seen in FIG. 3, Ti values were substantially lower at the +5 and +30 min time-points post-fentanyl in the GSHee-treated rats whereas Te values were equivalent to pre-values at both times, reinforcing the general observation that GSHee differentially effects the ventilatory effects of fentanyl.

Under physiological circumstances, the ratio of Vt/Ti is an accepted index of inspiratory drive although it could be argued that changes in PIF could be taken as a similar index of changes in inspiratory drive. However, the changes in Vt/Ti and PIF elicited by GSHee were not exactly the same (GSHee caused an initial transient spike in Vt/Ti not seen in PIF) although Vt/Ti and PIF both rose steadily between 5 to 15 min following injection. The injection of fentanyl elicited robust and long-lasting decreases in both Vt/Ti and PIF in vehicle-treated rats. However, it is clear that the depressant effects of fentanyl on PIF in the GSHee-treated rats were substantially less than the effects on Vt/Ti. As such, one possible interpretation of these findings is that GSHee does not entirely blunt the processes by which fentanyl suppresses inspiratory drive (Vt/Ti) it does have more pronounced effects on the processes by which fentanyl suppresses PIF.

Another compelling finding was that GSHee markedly reduced the occurrence of non-eupneic breaths (usually expressed as apneas, type 1 and 2 sighs) despite actually increasing fr, which usually is a stimulus to enhance non-eupneic breathing. This would tentatively suggest that GSHee exerts positive effects in brain regions such as the Kölliker-Fuse and pre-Botzinger complex, which generate/control rhythmic breathing, although to our knowledge there is no reports as to the direct effects of GSH in these neuronal complexes. With respect to the rejection index, it must be noted that the summation of sighs and apneas under non-eupneic breathing under the rejection index is obviously simplistic and does not do justice to the different mechanisms that elicit these individual respiratory patterns. Sighs are reported to result from activation of a neuronal circuit in the preBotzinger complex/parafacial group while apnea results from direct inhibition of the preBotzinger complex or inhibition of drive to phase-switching neurons in the pre-Botzinger complex. An increase in respiratory drive elicited by GSGee may decrease the number of sighs and decrease the number of apneas, but that would not be defined definitively by a change in the rejection index since this index also includes sniffs and changes in respiratory waveforms due to behavioral movements, although it must be noted that the fentanyl-treated rats (those that received vehicle or GSHee) were basically immobile throughout the ventilatory study. The ventilatory effects of GSHee resulted in predictable (minor) changes in ABG chemistry including an increase in pH, a decrease in $pCO_2$ and an increase in $pO_2$. There was minimal change in A-a gradient suggesting that GSHee did not directly affect gas-exchange processes in the lungs.

The injection of fentanyl to vehicle (saline)-pretreated rats elicited a sustained reduction in fr that was associated with pronounced long-lasting increases in Ti and EIP (at least 60 min) and pronounced but shorter-lived increases in Te and EEP (about 15 min in duration). Fentanyl also elicited a marked and sustained (at least 60 min) decrease in Vt (coupled to the decrease in fr resulting in a marked decrease in Ve), inspiratory drive (Vt/Ti), PIF and PEF. Finally, fentanyl caused a marked increase in Rejection Index (elevated disordered breathing) for 10-15 min. The potential sites and mechanisms of action underlying these effects of fentanyl have been addressed in detail elsewhere. Consistent with our previous study, the injection of fentanyl was associated with minor increases in BT that would have minimal direct effects on breathing.

Our major findings were that the ventilatory depressant effects and negative changes in ABG chemistry and A-a gradient elicited by fentanyl were markedly attenuated in rats pretreated with GSHee. With respect to fr, it would be easy to conclude that fentanyl still exerts dramatic effects since fentanyl elicited a rather precipitous fall in fr even though the values did not fall below baseline values. GSHee had little effect on the increase in Ti elicited by fentanyl. However, GSHee had a dramatic impact on the duration of fentanyl-induced increase in Te. Indeed, the substantially smaller fentanyl-induced increase in Te in the presence of GSHee suggests that GSHee enhances the central processes driving the end of expiration (inspiratory on-switch) and thus decrease expiratory duration. In addition, the thiolester may directly combat the ability of fentanyl to suppress the central processes driving expiration under fentanyl-induced hypoxic/hypercapnic conditions and/or the direct inhibitory effects of fentanyl on expiratory muscle activity, although it should be noted that there is evidence that opioids can actually increase expiratory muscle activity under certain circumstances. The effects of GSHee on the ability of fentanyl to lower PIF and PEF may also provide some discrimination as to potential sites and mechanisms of action of the thiolester. Remembering that GSHee elicited sustained increases in PIF and PEF, it was evident that fentanyl was able to elicit strong reductions in these parameters. The difference was that PIF fell to levels approximately equivalent to baseline values (before any drug was given) whereas the fentanyl-induced reduction in PEF was short-lived and PEF rapidly returned to the elevated levels seen after injection of GSHee. As such, it is possible that GSH-dependent processes may be more influential on central and peripheral mechanisms driving expiratory chest-muscles than inspiratory chest-muscles.

Opioid analgesics (e.g., fentanyl, morphine, etorphine, buprenorphine, methadone, butorphanol, oxymor-phone) have been demonstrated to increase A-a gradient in a variety of species including humans, goats, rabbits, dogs, impala, and rats. Opioids increase A-a gradients by impairing ventilation-perfusion ratios in the lungs (ventilation-perfusion mismatch). For example, opioids decrease pulmonary perfusion via hypoxia-induced pulmonary vasoconstriction, and by direct pulmonary vasoconstriction by mechanisms including centrally-mediated activation of sympathetic nerve activity to the lungs, and induction of histamine release in the lungs. As such, the ability of GSHee to overcome the fentanyl-induced increase in A-a gradient is most likely due to the direct GSHee-induced increase in Ve and potentially by interfering with any of the other mechanisms described immediately above.

The possibility that GSHee directly blunted the mechanisms by which fentanyl depressed breathing is supported by the evidence that GSHee did not affect baseline Vt values but markedly blunted the magnitude and duration of fentanyl-induced reduction fentanyl-induced reduction in Vt. This effect on Vt suggests that GSHee or its functional metabolites/nitrosylated species block central and peripheral signaling pathways by which fentanyl suppresses Vt. This key effect of GSHee is connected to the findings that GSHee reduced the ability of fentanyl to lower pH, $pO_2$ and $sO_2$ while elevating $pCO_2$ (all consistent with a fall in Ve) and blunted the fentanyl-induced increase A-a-gradient (i.e., impaired gas-exchange in the lungs). The ability GSHee to suppress fentanyl-induced disordered (non-eupneic) breathing raises the possibility that GSH-dependent mechanisms in key brainstem sites responsible for the control of breathing may be recruited to prevent the negative effects of fentanyl on eupneic breathing. An important consideration with respect to the ability of GSHee to prevent the deleterious effects of fentanyl on breathing was that the opioid appeared to elicit its full sedative effects in the presence of the GSHee (e.g., righting-reflex times and general observations of behavior could not discriminate between the effects of fentanyl in vehicle-treated or GSHee-treated rats). It could be expected that abrupt arousal may have led to enhanced breathing but as this did not appear to happen it is likely that GSHee interacted directly with the neural pathways/cellular mechanisms responsible for fentanyl-induced OIRD.

In summary, GSHee is a novel thiolester compound that is able to effectively prevent the ventilatory depressant effects of powerful opioids such as fentanyl (and other high potency opioids, such as sufentanil and alfentanil) and their deleterious effects on breathing stability and gas-exchange within the lungs without compromising the analgesic actions of the opioids. The ability of GSHee to prevent the negative effects of fentanyl on Vt is a key factor in the therapeutic potential of this thiolester in the treatment of OIRD. The administration protocol used in this Example highlights the ability of GSHee to affect ventilatory parameters and to blunt the negative effects of fentanyl on breathing.

Pretreatment with GSHee blunted the effects of the subsequent injection of fentanyl in a manner that suggest that the actions are heavily dependent on the actions of fentanyl itself on some parameters but not others. More specifically, pretreatment with GSHee elicited a sustained attenuation of the long-lasting negative effects of fentanyl on Vt, Vt/Ti and PIF whereas it had relatively minimal effects on the long-lasting effects of fentanyl on Ti and EIP. In addition, pretreatment with GSHee elicited a pronounced attenuation of the relatively short-lived effects of fentanyl on fr and Te, EEP and Rejection Index. As such, it is evident the GSHee reaches the systems/circuitry that are involved in some of the actions of fentanyl but not others.

GSHee could be an addition to the important strategy to mitigate OIRD via co-treatment with non-OR ventilatory stimulants that do not affect opioid-induced analgesia. Several classes of non-OR ventilatory stimulants are currently being investigated with many acting in the brainstem respiratory network including Dl-dopamine receptor agonists, 5-hydroxytryptamine receptor modulators, a-amino-3-hydroxy-5-methyl-4-isoxazolepropionic acid receptor agonists (ampakines), thyrotropin-releasing hormone, the endogenous peptide glycyl-glutamine, and phospodiesterase-4 inhibitors. Others include doxapram and GAL021 that act on K+-channels on $O_2$-sensing cells of the carotid bodies.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of stimulating ventilatory and/or respiratory drive in a subject in need thereof, the method comprising: administering to the subject a therapeutically effective amount of a composition comprising a glutathione alkyl ester, adduct thereof, or pharmaceutically acceptable salt, tautomer, or solvate thereof, wherein the adduct of the glutathione alkyl ester is at least one of an albumin adduct, a glucose adduct, an L-cysteine adduct, a D-cysteine adduct, and an S-nitroso adduct.

2. The method of claim 1, wherein the glutathione alkyl ester is a compound having the structure of the formula:

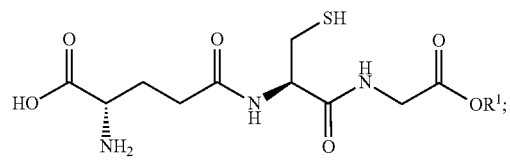

where $R^1$ is an unsubstituted or substituted lower alkyl ($C_1$-$C_6$ alkyl) or pharmaceutically acceptable salts, tautomers, or solvates thereof.

3. The method of claim 1, wherein the glutathione alkyl ester is an L-glutathione alkyl ester, adduct thereof, or pharmaceutically acceptable salt, tautomer, or solvate thereof.

4. The method of claim 1, wherein the therapeutically effective amount is an amount effective to stimulate the ventilatory and/or respiratory drive of the subject, increase tidal volume, increase respiratory frequency, increase minute ventilation, increase peak inspiratory flow, increase inspiratory drive, and/or increase Alveolar-arterial (A-a) gradient.

5. The method of claim 1, wherein the subject has or is at increased risk of respiratory depression, sleep apnea, apnea of prematurity, obesity-hyperventilation syndrome, primary alveolar hypoventilation syndrome, dyspnea, altitude sickness, hypoxia, hypercapnia, cystic fibrosis, and chronic obstructive pulmonary disease (COPD).

6. The method of claim 1, wherein the subject has or is at increased risk of respiratory depression, wherein the respiratory depression is caused by anesthetic, a sedative, anxiolytic agent, a hypnotic agent, alcohol, and/or a narcotic.

7. The method of claim 6, wherein the narcotic is an opioid.

8. The method of claim 7, wherein the opioid is fentanyl or morphine.

9. The method of claim 1, further comprising administering at least one additional composition selected from the group consisting of an opioid, doxapram and enantiomers thereof, acetazolamide, almitrine, GAL021, theophylline, caffeine, methylprogesterone and related compounds, sedatives that decrease arousal threshold in sleep disordered breathing patients, sodium oxybate, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, and combinations thereof.

* * * * *